(12) United States Patent
Giarola et al.

(10) Patent No.: US 12,083,342 B2
(45) Date of Patent: *Sep. 10, 2024

(54) NEUROMODULATION DEVICE

(71) Applicants: Galvani Bioelectronics Limited, Middlesex (GB); Case Western Reserve University, Cleveland, OH (US)

(72) Inventors: Alessandra Giarola, Stevenage (GB); Yee-Hsee Hsieh, Cleveland, OH (US); Stephen J. Lewis, Cleveland, OH (US); Arun Sridhar, Stevenage (GB)

(73) Assignees: Galvani Bioelectronics Limited (GB); Case Western Reserve University, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 17/883,332

(22) Filed: Aug. 8, 2022

(65) Prior Publication Data

US 2023/0017399 A1   Jan. 19, 2023

Related U.S. Application Data

(63) Continuation of application No. 16/080,203, filed as application No. PCT/IB2017/051143 on Feb. 27, 2017, now Pat. No. 11,452,872.

(60) Provisional application No. 62/301,198, filed on Feb. 29, 2016.

(51) Int. Cl.
| | |
|---|---|
| *A61N 1/36* | (2006.01) |
| *A61B 5/00* | (2006.01) |
| *A61B 5/08* | (2006.01) |
| *A61N 1/00* | (2006.01) |

(Continued)

(52) U.S. Cl.
CPC ........ *A61N 1/3611* (2013.01); *A61B 5/0826* (2013.01); *A61B 5/4818* (2013.01); *A61N 1/00* (2013.01); *A61N 1/0556* (2013.01); *A61N 1/18* (2013.01); *A61N 1/36* (2013.01)

(58) Field of Classification Search
CPC ...... A61N 1/3611; A61N 1/00; A61N 1/0556; A61N 1/18; A61N 1/36; A61B 5/0826
See application file for complete search history.

(56) References Cited

U.S. PATENT DOCUMENTS

| | | | |
|---|---|---|---|
| 7,149,574 B2 * | 12/2006 | Yun | A61N 1/36189 607/2 |
| 7,650,189 B1 | 1/2010 | Park et al. | |
| 8,103,341 B2 | 1/2012 | Libbus et al. | |

(Continued)

FOREIGN PATENT DOCUMENTS

WO    2010-059839 A2    5/2010

OTHER PUBLICATIONS

A. Ofri et al., Horner's Syndrome in Traumatic First Rib Fracture without Carotid Injury; Review of Anatomy and Pathphysiology Trauma Case Reports, vol. 8, 2017, pp. 1-4, ISSN 2352-6440 (2017).

*Primary Examiner* — Shirley X Jian
(74) *Attorney, Agent, or Firm* — McAndrews, Held & Malloy, Ltd.

(57) ABSTRACT

This disclosure provides an apparatus or system for the modulation of neural activity in the cervical sympathetic chain (CSC) or superior cervical ganglion (SCG) or SCG post-ganglionic branch(es) and for the treatment of sleep apnoea, as well as methods for their use.

17 Claims, 22 Drawing Sheets

(51) Int. Cl.
*A61N 1/05* (2006.01)
*A61N 1/18* (2006.01)

(56) References Cited

U.S. PATENT DOCUMENTS

| | | |
|---|---|---|
| 8,155,744 B2 | 4/2012 | Rezai |
| 8,229,564 B2 | 7/2012 | Rezai |
| 8,527,042 B2 | 9/2013 | Libbus et al. |
| 8,691,877 B2 * | 4/2014 | Yun ................ A61K 31/4188 607/2 |
| 8,718,790 B2 | 5/2014 | Pianca |
| 8,788,041 B2 * | 7/2014 | Yun ................ A61M 5/14276 607/40 |
| 8,897,881 B2 | 11/2014 | Libbus et al. |
| 10,716,749 B2 * | 7/2020 | Yun ...................... A61K 9/0034 |
| 2004/0249416 A1 * | 12/2004 | Yun .................... A61N 1/36189 607/2 |
| 2005/0085874 A1 | 4/2005 | Davis et al. |
| 2006/0224211 A1 | 10/2006 | Durand et al. |
| 2008/0208305 A1 | 8/2008 | Rezai et al. |
| 2009/0155336 A1 | 6/2009 | Rezai |
| 2009/0287265 A1 | 11/2009 | Henke |
| 2010/0094379 A1 * | 4/2010 | Meadows .......... A61N 1/37264 607/48 |
| 2014/0046407 A1 | 2/2014 | Ben-Ezra et al. |
| 2016/0263376 A1 * | 9/2016 | Yoo ...................... A61N 1/36017 |
| 2018/0056074 A1 | 3/2018 | Clark et al. |
| 2019/0001139 A1 | 1/2019 | Mishra et al. |
| 2019/0201684 A1 | 7/2019 | Williams et al. |
| 2020/0246622 A1 * | 8/2020 | Sridhar ............. A61N 1/36178 |

\* cited by examiner

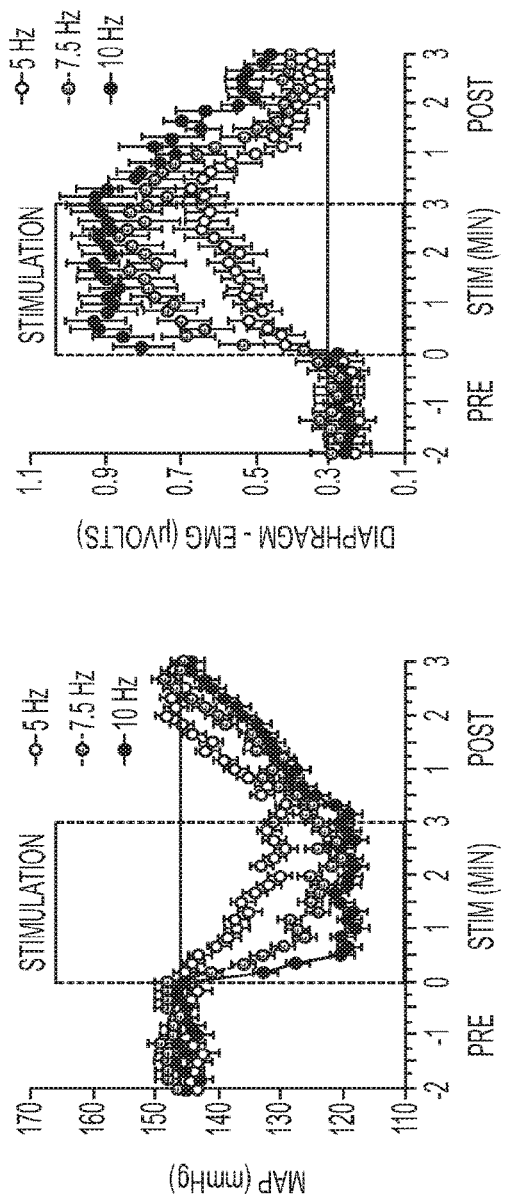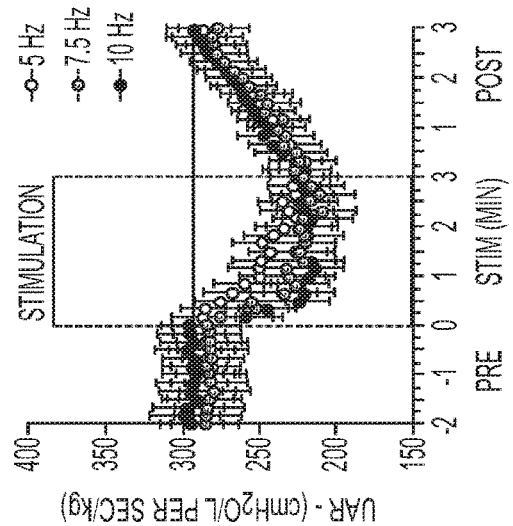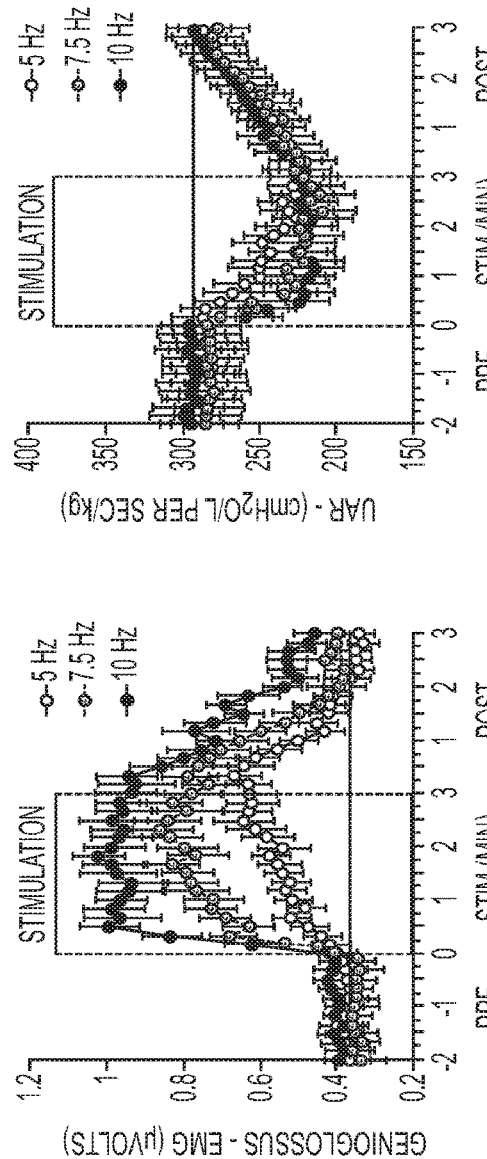

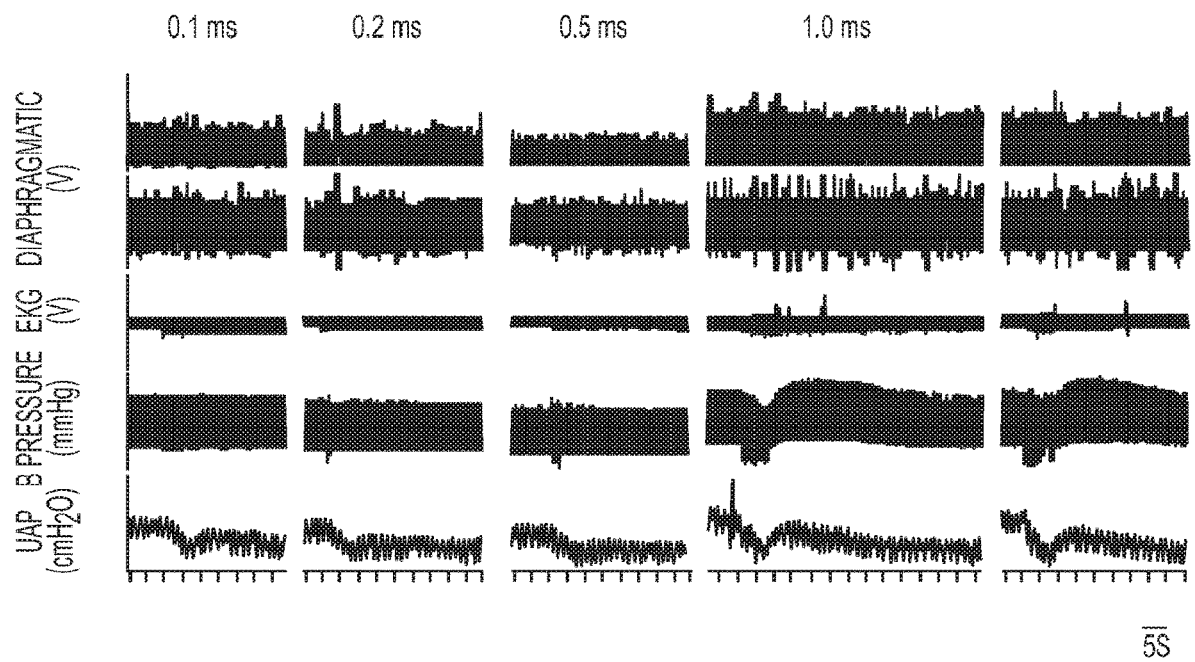
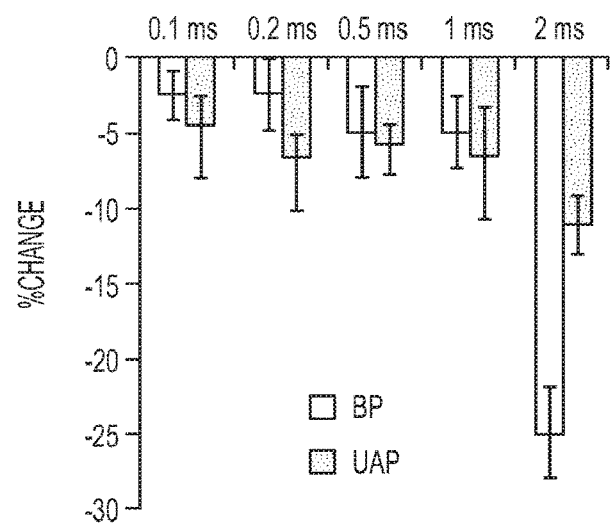
FIG. 15

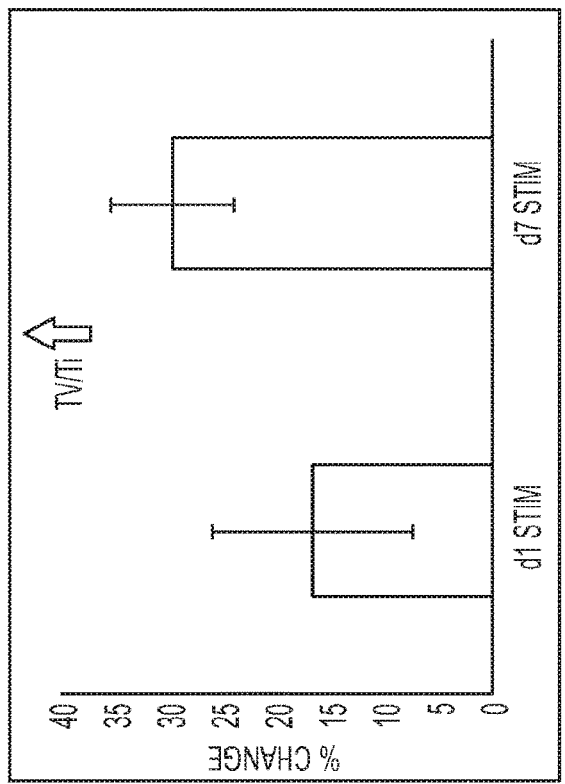
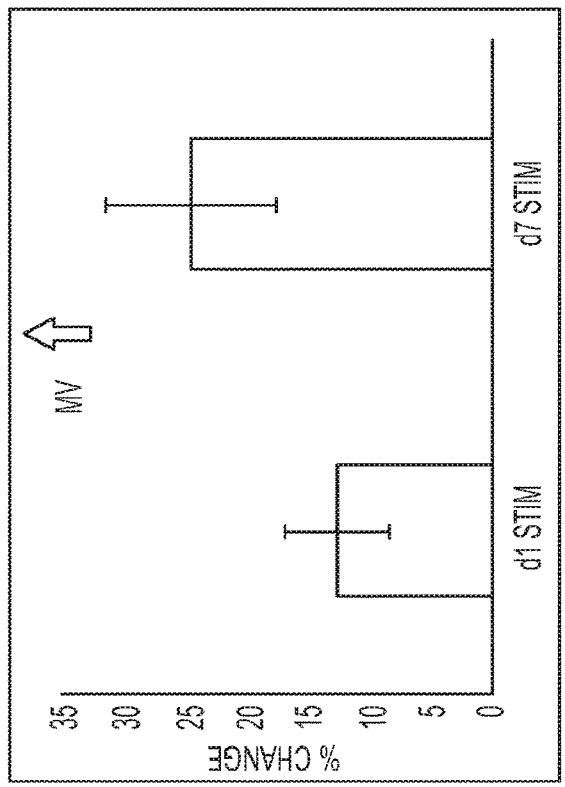
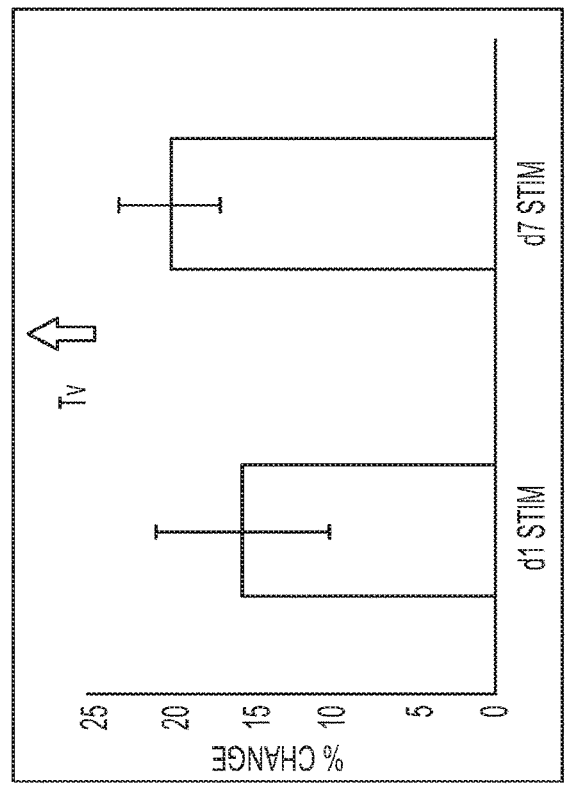
FIG. 19

NEUROMODULATION DEVICE

CROSS-REFERENCE TO RELATED APPLICATIONS

This application is a continuation of U.S. patent application Ser. No. 16/080,203 filed Aug. 27, 2018, which is a U.S. National Stage application under 35 U.S.C. § 371 of International Application PCT/IB2017/051143 (published as WO 2017/149436 A1) filed Feb. 27, 2017, which claims the benefit of priority to U.S. provisional Application No. 62/301,198 filed Feb. 29, 2016. Each of these prior applications are hereby incorporated by reference in their entirety.

BACKGROUND

Sleep apnoea is a condition in which normal breathing is interspersed by episodes of complete ventilatory silence and/or erratic (non-eupnoeic) breathing. These episodes of sleep apnoea and erratic breathing typically occur during the rapid-eye movement (REM) phase of the sleep cycle. Symptoms of sleep apnoea include fatigue, cognitive impairment (for example slower reaction time, impaired memory), hypertension, and vision problems.

Sleep apnoea may be classified as central sleep apnoea or obstructive sleep apnoea, with many subjects having both. Central sleep apnoea (CSA) is due to inadequate neural control of respiratory muscles and lack of respiratory drive. Obstructive Sleep Apnoea (OSA) is a disorder characterised by repetitive collapse and reopening of the upper airway during sleep, which impairs ventilation and can result in intermittent hypoxemia and hypercapnia. OSA is a multi-factorial disorder and the pathophysiological factors that contribute to OSA include reduced upper airway dilator muscle activity during sleep, upper airway anatomical features that vary from normal, insufficient ventilatory control and diminished lung volume. OSA has been shown to be a major risk factor for developing diabetes, hypertension, atrial fibrillation, heart failure and sudden death.

Ventilation is a neurally and mechanically active (inspiration) and passive (expiration) process. The involuntary control of breathing is driven by the respiratory neural network in the brainstem and is in part mediated via increased activity of diaphragmatic and chest-wall muscles (via increased drive from the phrenic and intercostal nerves).

Attempts to treat CSA have included diaphragmatic pacing. Such pacing uses a device which stimulates the phrenic nerve (motor nerve driving the diaphragm) via an intravascular lead. Attempts to treat OSA have included hypoglossal nerve stimulation, using a closed-loop reactive unit that triggers stimulation of the hypoglossal nerve upon detection of absence of chest movement (using an impedance sensor).

SUMMARY OF INVENTION

The present disclosure describes an apparatus or system for treating sleep apnoea in a subject. The apparatus or system includes at least one neural interfacing element configured to deliver a signal to at least one cervical sympathetic chain ("CSC"), superior cervical ganglion (SCG) and/or a postganglionic branch thereof of the subject; and a controller operably coupled to the neural interfacing element. The controller programs the neural interfacing element to deliver a signal that increases localized sympathetic activity of the CSC, SCG and/or a postganglionic branch thereof, thereby increasing sympathetic activity of the CSC, SCG and/or a postganglionic branch thereof and ameliorating sleep apnoea in the subject.

Also described is an apparatus or system for modulating the neural activity of a CSC, SCG and/or a postganglionic branch thereof of a subject. The apparatus or system includes a neural interfacing element having one or more transducers each configured to apply a signal to a CSC, SCG and/or a postganglionic branch thereof of the subject; and a controller operably coupled to the one or more transducers. The controller controlling the signal to be applied by the transducer(s), such that the signal stimulates increased localized sympathetic neural activity in the CSC, SCG and/or a postganglionic branch thereof. Said increase in localized sympathetic activity is then able to produce a physiological response in the subject.

Optionally, the neural interfacing element is configured to deliver a signal to the superior cervical ganglia ("SCG") and/or one or more post-ganglionic branch(es) thereof. Optionally, two or more neural interfacing elements (e.g., two or more transducers) are positioned bilaterally to increase localized sympathetic activity of the right and left CSC, SCG and/or a postganglionic branch thereof.

Favourably, the neural interfacing element is implantable. Such an implantable neural interfacing element is preferably less than 1 cc in size.

Also described are methods for increasing sympathetic activity in a CSC, SCG and/or a postganglionic branch thereof of a subject. The method involves: i) implanting in the subject at least a portion of an apparatus or system as disclosed herein; ii) positioning at least one neural interfacing element (e.g., a transducer) of the apparatus or system in signalling contact with a CSC, SCG and/or a postganglionic branch thereof of the subject; and iii) activating the apparatus or system.

Favourably, the method ameliorates sleep apnoea in a subject, and thus is a method of treating sleep apnoea in a patient. As indicated above, such methods involve delivering a signal to a CSC, SCG and/or a postganglionic branch thereof of the subject to stimulate neural activity in the nerve.

Also described herein is a method of treating sleep apnoea in a subject, the method comprising delivering a signal to a CSC, SCG and/or a postganglionic branch thereof of the subject to stimulate neural activity in said CSC, SCG and/or a postganglionic branch thereof in the subject. Optionally the signal is delivered by a neural interfacing element (e.g. a transducer) of an apparatus or system as described herein. Optionally the signal is delivered to a SCG and/or post-ganglionic branch(es) of the SCG in the subject. Optionally the signal is delivered unilaterally (to the left or right CSC, SCG and/or a postganglionic branch thereof), or bilaterally.

Also disclosed are neuromodulatory electrical waveforms for use in treating sleep apnoea in a subject. Such waveforms are an alternating current (AC) or direct current (DC) waveform having a frequency of 1-50 Hz, such that, when applied to a CSC, SCG and/or a postganglionic branch thereof, the waveform stimulates neural signalling in the nerve.

Also disclosed is the use of a neuromodulation device for treating sleep apnoea in a subject by stimulating neural activity in a CSC, SCG and/or a postganglionic branch thereof of the subject.

In a preferred embodiment of all aspects of the invention, the subject is a human, e.g., a patient experiencing or suffering from sleep apnoea.

BRIEF DESCRIPTION OF THE FIGURES

FIGS. 2A and 2B show the glossopharyngeal nerve, carotid sinus nerve and carotid body. FIG. 2A shows the jugular and nodose ganglia and branches of the vagus (black). FIG. 2B shows the superior cervical ganglion and major branches (stippled). The names of arteries (A) present in both drawings are given in FIG. 2B. Reconstruction from serial sections. Approximate magnification×17.

FIG. 2C shows nerves near the ventrolateral third of the carotid body, FIG. 2D shows the middle third, and FIG. 2E shows the dorsomedial third. The arrow in FIG. 2C marks an anastomosis between the sinus nerve and a sympathetic nerve. FIG. 2D illustrates the sympathetic nerves that surround the carotid body artery. FIG. 2E shows the ganglioglomerular nerve as branches of the external carotid nerve that project to the carotid body. Approximate magnification×80. (Taken from McDonald D. M. 12: 345-372, 1983).

FIGS. 5A-5D: Changes in mean arterial blood pressure (MAP, FIG. 5A, top left panel), diaphragmatic muscle EMG (FIG. 5B, top right), genioglossus muscle EMG (FIG. 5C, bottom left) and upper airway resistance (UAR, FIG. 5D, bottom right), elicited by 5, 7.5 and 10 Hz concurrent electrical stimulation (10V, 2 ms) of both cervical sympathetic chains in sevoflurane-anesthetized Spontaneously Hypertensive rats. The data are presented as mean±SEM. There were 12 rats in each group.

FIG. 15: Bilateral stimulation of CSC. Changes in stimulation pulse width differentially impacted Blood Pressure (BP) and upper airway pressure (n=5). Percentage change calculated versus each rat prior to stimulation.

FIG. 19: Whole body plethysmography chamber was used to assess changes in number of disordered breathing after bilateral intermittent CSC stimulation (0.5 mA, 5 Hz, 0.2 ms) for 1 day and after 7 days. Conscious freely moving Zucker Fat (14 wks) male rats, n=3.

DETAILED DESCRIPTION

The effectiveness of inspiration and expiration is critically-dependent on, among a variety of factors, the patency and open-status (position of the tongue) of the upper airway. Therefore, the tongue (genioglossus) and oropharyngeal muscles as well as motor drive to these muscles have a critical role in determining upper airway patency. The involuntary control of breathing can be modulated by (1) descending input from higher brain centres (e.g., prefrontal cortex, hypothalamus) into the brainstem to allow for adjustments in breathing that are required to match the physiological requirements of the body, and (2) peripheral chemoreceptors emanating from the carotid bodies (which continually sample arterial blood $pCO_2$, pH and $pCO_2$ levels) to alert the brainstem respiratory control centres as to any changes in arterial blood-gas chemistry. The carotid bodies detect hypoxic episodes such as those occurring during sleep apnoea to trigger afferent signals that adjust central respiratory drive.

Figure 1:
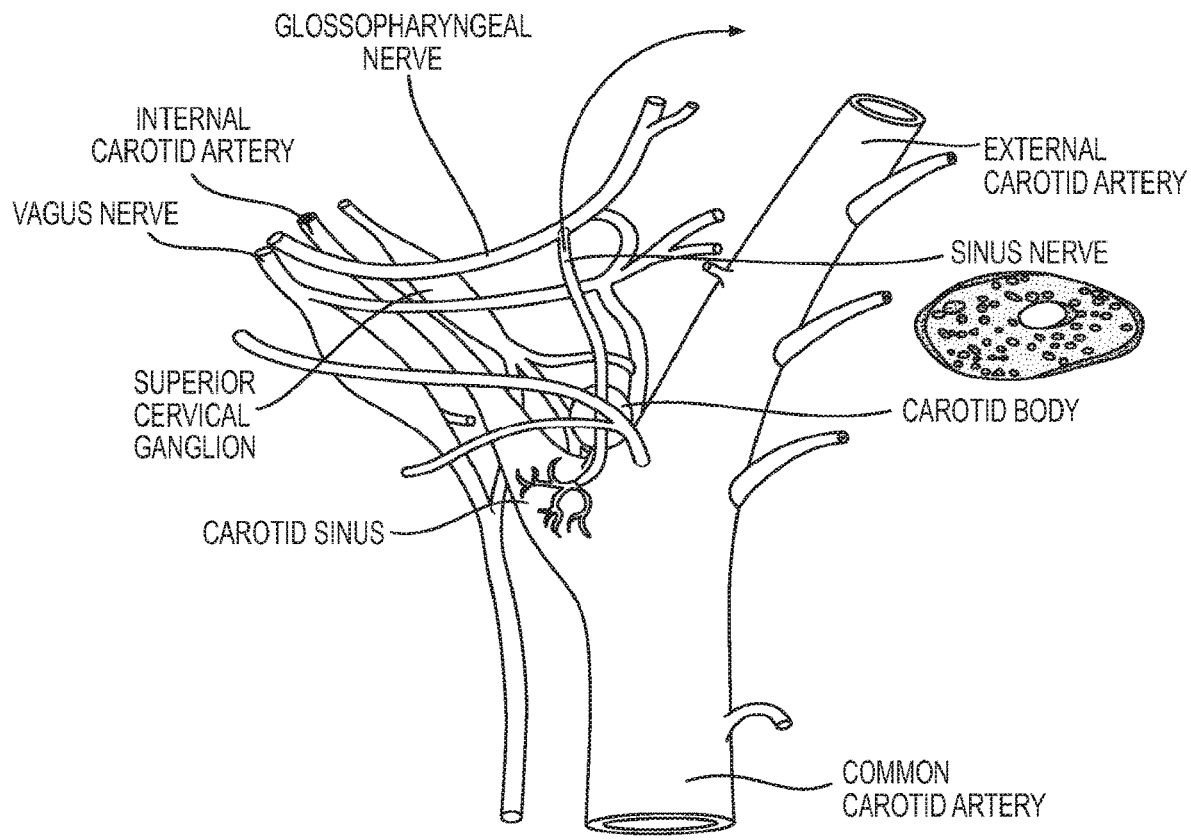
FIG. 1: Relationship between the superior cervical ganglion and the carotid sinus nerve: (Adapted from McDonald D. M. 12: 345-372, 1983). Cervical sympathetic chain provides post-ganglionic sympathetic fibres to carotid sinus nerve.
Figure 2A:
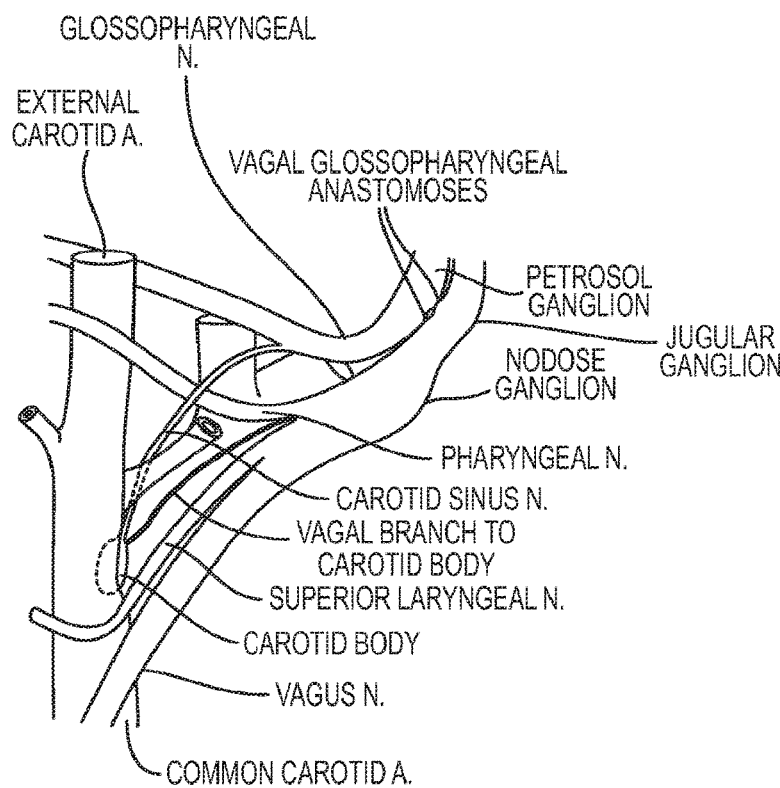
FIGS. 2A and 2B. Drawings of the ventrolateral aspect of the bifurcation of a left common carotid artery. The panels show major nerves (N) and ganglia in the region of the carotid sinus nerve.
Figure 2B:
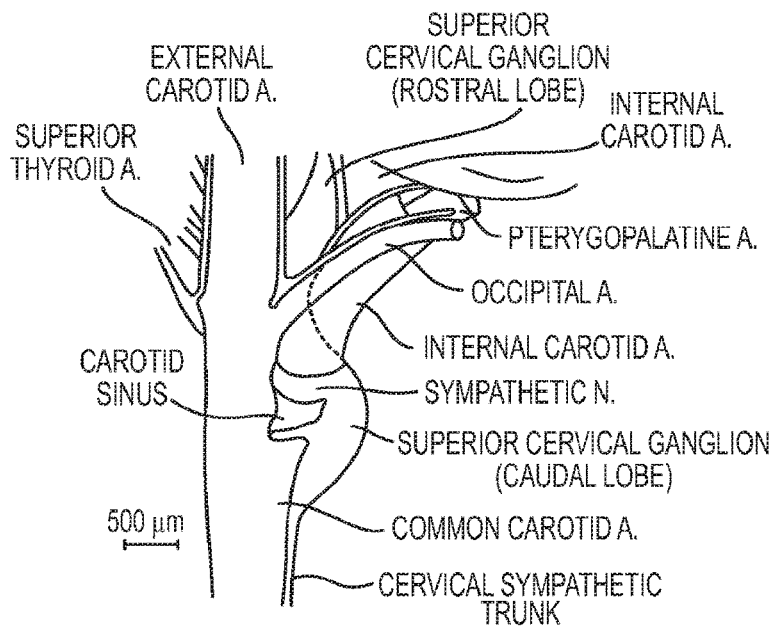
Figure 2C:
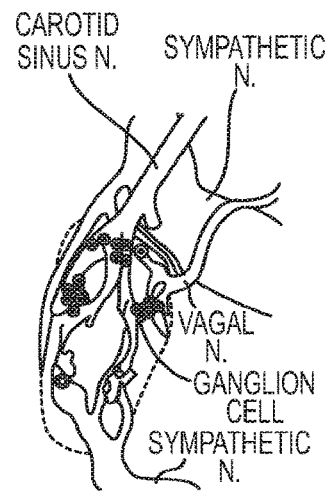
FIGS. 2C-2E. Drawings of the carotid body (broken line) shown in FIGS. 2A and 2B illustrating additional features of the relationship of the sinus nerve, sympathetic nerves and a branch from the vagus nerve. Also shown are locations of ganglion cells associated with each nerve.
Figure 2D:
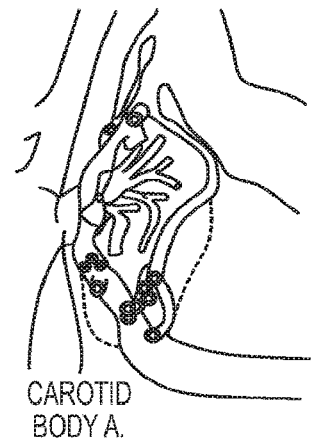
Figure 2E:
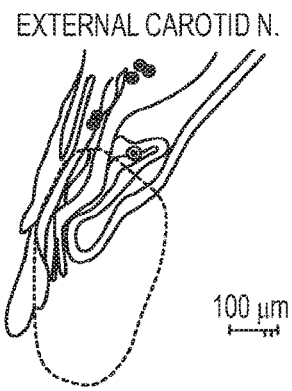

The superior cervical ganglia (SCG) are bilateral structures that reside in close proximity to the carotid body at the trifurcation of the common carotid artery into the internal and external carotid arteries and the occipital artery (FIG. 1). The SCG contains the cell bodies of post-ganglionic sympathetic neurons that project to a variety of structures in the brain (e.g., hypothalamus) in addition to the upper airways (e.g., larynx), tongue, and salivary glands (e.g., submandibular gland) as well as the phrenic nerves innervating the diaphragm, and the carotid sinus nerves that innervate primary *glomus* cells (which sense blood $pO_2$, $pCO_2$ and pH levels) in the carotid bodies (shown in greater detail in FIGS. 2A-2E). Pre-ganglionic projections in the spine (C1-C4) project to post-ganglionic neurons in each SCG via an ipsilateral cervical sympathetic chain (CSC). The CSC thus comprises pre-ganglionic neurons projecting into the SCG. The SCG also includes the cell bodies of the post-ganglionic neurons, the axons of which project from the SCG. Stimulation of a CSC thereby increases neural activity of the ipsilateral SCG, in particular in the postganglionic neurons thereof. The whole of the CSC, SCG and postganglionic neurons thereof go to form the CSC-SCG complex (or CSC-SCG).

The inventors identified that the CSC-SCG complex is well placed to modulate a variety of physiological functions playing important roles in sleep apnoea. As demonstrated herein, stimulation of the CSC-SCG complex unilaterally (right or left) or bilaterally is able to induce improvements in a range of sleep apnoea associated functions, including blood pressure, diaphragmatic muscle activity, genioglossus muscle (tongue) activity and position, airway resistance, and the frequency and duration of disordered apnoeic breaths. These effects are not observed following hypoglossal nerve stimulation.

Moreover, it is identified herein that different physiological responses can be induced depending on whether stimulation is unilateral (right), unilateral (left), or bilateral. Thus, advantageously, one range of responses can be induced by unilateral (left) stimulation, for example a decrease in blood pressure; a second range of responses can be induced by unilateral (right) stimulation, for example a decrease in respiratory rate/increase in tidal volume; and a third range of responses induced by bilateral stimulation, for example a decrease in blood pressure and a decrease in respiratory rate/increase in tidal volume. Similarly, it is demonstrated herein that different physiological responses can be induced depending on the nature of the signal (for example, for an electrical signal, by varying the frequency and/or pulse duration). For example, different reductions in airway resistance and/or blood pressure can be induced depending on the nature of the signal applied. This differentiation of effects allows the appropriate stimulation to be matched to the symptoms exhibited by the subject at any given time.

This disclosure describes an apparatus and/or system for the treatment of sleep apnoea, as well as methods for treating sleep apnoea, in a subject.

The terms as used herein are given their conventional definition in the art as understood by the skilled person, unless otherwise defined below. In the case of any inconsistency or doubt, the definition as provided herein should take precedence.

As used herein, application of a signal may equate to the transfer of energy in a suitable form to carry out the intended effect of the signal. That is, application of a signal to a nerve or nerves may equate to the transfer of energy to (or from) the nerve(s) to carry out the intended effect. For example, the energy transferred may be electrical, mechanical (including acoustic, such as ultrasound), electromagnetic (e.g. optical), magnetic or thermal energy. It is noted that application of a signal as used herein does not include a pharmaceutical intervention.

As used herein, "neural interfacing element" is taken to mean any element (e.g., a "transducer") for applying a signal to the nerve, for example an electrode, diode, Peltier element or ultrasound transducer.

As used herein, "neural activity" of a nerve is taken to mean the signalling activity of the nerve, for example the amplitude, frequency and/or pattern of action potentials in the nerve. "Sympathetic activity" is taken to mean signalling activity in a sympathetic nerve. "Localized sympathetic activity" is sympathetic activity local to the nerve in which activity is stimulated sympathetic activity in the stimulated nerve and those neurons downstream of the stimulated nerve. For example, localized sympathetic activity following stimulation of the CSC can include sympathetic activity in the CSC and also in the SCG and/or a postganglionic neuron thereof.

Modulation of neural activity, as used herein, is taken to mean that the signalling activity of the nerve is altered from the baseline neural activity—that is, the signaling activity of the nerve in the subject prior to any intervention. Such modulation may increase (i.e. stimulate), inhibit (for example block), or otherwise change the neural activity compared to baseline activity. In preferred embodiments of the invention, the modulation is stimulation of neural activity, in particular sympathetic activity.

Stimulation of neural activity (for example stimulation of sympathetic activity) is an increase in neural activity, this may be an increase in the total signalling activity of the whole nerve, or that the total signalling activity of a subset of nerve fibres of the nerve is increased, compared to baseline neural activity in that part of the nerve.

Modulation of neural activity may also be an alteration in the pattern of action potentials. It will be appreciated that the pattern of action potentials can be modulated without necessarily changing the overall frequency or amplitude. For example, modulation of the neural activity may be such that the pattern of action potentials is altered to more closely resemble a healthy state rather than a disease state.

Modulation of neural activity may comprise altering the neural activity in various other ways, for example increasing or inhibiting a particular part of the neural activity and/or stimulating new elements of activity, for example in particular intervals of time, in particular frequency bands, according to particular patterns and so forth. Such altering of neural activity may for example represent both increases and/or decreases with respect to the baseline activity.

Modulation of the neural activity may be temporary. As used herein, "temporary" is taken to mean that the modulated neural activity (whether that is an increase, inhibition, block or other modulation of neural activity or change in pattern versus baseline activity) is not permanent. That is, the neural activity following cessation of the signal is substantially the same as the neural activity prior to the signal being applied—i.e. prior to modulation.

Modulation of the neural activity may be persistent. As used herein, "persistent" is taken to mean that the modulated neural activity (whether that is an increase, inhibition, block or other modulation of neural activity or change in pattern versus baseline activity) has a prolonged effect. That is, upon cessation of the signal, neural activity in the nerve remains substantially the same as when the signal was being applied—i.e. the neural activity during and following modulation is substantially the same.

Modulation of the neural activity may be corrective. As used herein, "corrective" is taken to mean that the modulated neural activity (whether that is an increase, inhibition, block or other modulation of neural activity or change in pattern versus baseline activity) alters the neural activity towards the pattern of neural activity in a healthy individual. That is, upon cessation of the signal, neural activity in the nerve more closely resembles the pattern of action potentials in the nerve observed in a healthy subject than prior to modulation, preferably substantially fully resembles the pattern of action potentials in the nerve observed in a healthy subject.

Such corrective modulation caused by the signal can be any modulation as defined herein. For example, application of the signal may result in a block on neural activity, and upon cessation of the signal, the pattern of action potentials in the nerve resembles the pattern of action potentials observed in a healthy subject. By way of further example, application of the signal may result in modulation such that the neural activity resembles the pattern of action potentials observed in a healthy subject, and upon cessation of the signal, the pattern of action potentials in the nerve resembles the pattern of action potentials observed in a healthy individual.

As used herein, sleep apnoea (or sleep apnea) is used to refer to disorders characterised by interruptions in breathing during sleep and/or by shallow or infrequent breathing. "Sleep apnoea" is used to refer to both central sleep apnoea (CSA) and obstructive sleep apnoea (OSA) unless specified otherwise. An "apnoeic episode" is taken to mean a single disordered breath or interruption in breathing. Risk factors for sleep apnoea include (but are not limited to) obesity, smoking, nasopharyngeal anatomical abnormalities, neck size greater than 16 inches.

As used herein, the neural activity in the CSC-SCG (or a component thereof) of a healthy individual is that neural activity exhibited by a subject who does not have sleep apnoea.

As used herein, an "improvement in a measurable physiological parameter" is taken to mean that for any given physiological parameter, an improvement is a change in the value of that parameter in the subject towards the normal value or normal range for that value—i.e. towards the expected value in a healthy individual.

For an example, in a subject suffering from sleep apnoea, an improvement in measurable parameter may be one or more of: a decrease in systemic sympathetic tone, a decrease in duration of apnoeic episodes, a decrease in frequency of apnoeic episodes, a decrease in blood pressure (for example a decrease in mean arterial pressure), a decrease in respiratory rate, an increase in tidal volume, a decrease in upper airway resistance, an increase in diaphragmatic muscle activity (also referred to as diaphragmatic tone), an increase in genioglossus muscle activity (also referred to as genioglossus tone), an increase in central respiratory drive.

Techniques for measuring these parameters would be familiar to the skilled person. For example: systemic sympathetic tone can be determined by direct measurement of sympathetic nerve activity, by measurement of levels of urinary catecholamines, measurement of the sympatho-vagal balance via heart rate variability (lower heart rate variability being indicative of a decrease in sympathetic tone); frequency and duration of apnoeas can be determined during apnoeic sleep studies or by changes in chest wall impedence; blood pressure can be measured using invasive methods (e.g. arterial blood pressure) or non-invasive methods (e.g. blood pressure cuffs, sphygmomanometers); respiratory parameters (e.g. respiratory rate, respiratory drive, tidal volume, minute ventilation, peak inspiratory/expiratory flow, inspiration/expiration time, $EF_{50}$) can be measured by plethysmography; airway resistance can be determined using an airway perturbation device, a forced oscillation technique or a plethysmography device, or by end tidal $CO_2$; diaphragmatic muscle activity can be determined using an implanted EMG electrode; genioglossus muscle activity can be determined during sleep endoscopy or by EMG in anaesthetised subjects.

The physiological parameter may comprise an action potential or pattern of action potentials in a nerve of the subject. An improvement in such a parameter is characterised by the action potential or pattern of action potentials in the nerve more closely resembling that exhibited by a healthy individual than before the intervention.

As used herein, a physiological parameter is not affected by modulation of the neural activity if the parameter does not change as a result of the modulation from the average value of that parameter exhibited by the subject or patient when no intervention has been performed—i.e. it does not depart from the baseline value for that parameter.

The skilled person will appreciate that the baseline for any neural activity or physiological parameter in an individual need not be a fixed or specific value, but rather can fluctuate within a normal range or may be an average value with associated error and confidence intervals. Suitable methods for determining baseline values would be well known to the skilled person.

As used herein, a measurable physiological parameter is detected in a subject when the value for that parameter exhibited by the subject at the time of detection is determined. A detector is any element able to make such a determination.

A "predefined threshold value" for a physiological parameter is the value for that parameter where that value or beyond must be exhibited by a subject or patient before the intervention is applied. For any given parameter, the threshold value may be a value indicative of predisposition to sleep apnoea, and/or an imminent or ongoing episode of apnoea.

Examples of such predefined threshold values include sympathetic tone (neural, hemodynamic (e.g. heart rate, blood pressure, heart rate variability) or circulating plasma/urine biomarkers) greater than a threshold sympathetic tone, or greater than sympathetic tone in a healthy individual; diaphragmatic tone lower than a threshold diaphragmatic tone, or greater than diaphragmatic tone in a healthy individual; genioglossus tone lower than a threshold genioglossus tone, or greater than genioglossus tone in a healthy individual; blood pressure higher than that characteristic of a healthy individual; a respiratory rate higher than that characteristic of a healthy individual; a respiratory rate lower than that characteristic of a healthy individual; a central respiratory drive lower than that characteristic of a healthy individual; a tidal volume lower than that characteristic of a healthy individual; an upper airway resistance higher than that characteristic of a healthy individual. Appropriate values for any given parameter would be simply determined by the skilled person.

Such a threshold value for a given physiological parameter is exceeded if the value exhibited by the subject is beyond the threshold value—that is, the exhibited value is a greater departure from the normal or healthy value for that parameter than the predefined threshold value.

Treatment of sleep apnoea as used herein, for example treatment of CSA and/or treatment of OSA, is characterised by the subject exhibiting less frequent or less severe episodes of sleep apnoea than before treatment. Treatment may be characterised by amelioration of an ongoing apnoeic episode. For example, treatment may be applied when the subject is undergoing an apnoeic episode and results in at least partial relief of the apnoeic episode, preferably full relief of the apnoeic episode (i.e. a return to healthy breathing pattern). Treatment may be indicated by one or more of: a decrease in duration of apnoeic episodes, a decrease in frequency of apnoeic episodes, a decrease in blood pressure (for example a decrease in mean arterial pressure), a decrease in respiratory rate, an increase in tidal volume, a decrease in upper airway resistance, an increase in diaphragmatic muscle activity (also referred to as diaphragmatic tone), an increase in genioglossus muscle activity (also referred to as genioglossus tone).

A "neuromodulation device" or "neuromodulation apparatus" (used interchangeably) as used herein is a device or apparatus configured to modulate the neural activity of a nerve. Neuromodulation devices as described herein comprise at least one transducer capable of effectively applying a signal to a nerve. In those embodiments in which the neuromodulation device is at least partially implanted in the subject, the elements of the device that are to be implanted in the subject are constructed such that they are suitable for such implantation. Such suitable constructions would be well known to the skilled person. Indeed, various fully implantable neuromodulation devices are currently available, such as the vagus nerve stimulator of SetPoint Medical, in clinical development for the treatment of rheumatoid arthritis (*Arthritis & Rheumatism*, Volume 64, No. 10 (Supplement), page S195 (Abstract No. 451), October 2012. *"Pilot Study of Stimulation of the Cholinergic Anti-Inflammatory Pathway with an Implantable Vagus Nerve Stimulation Device in Subjects with Rheumatoid Arthritis"*, Frieda A. Koopman et al), and the INTERSTIM™ device (Medtronic, Inc), a fully implantable device utilised for sacral nerve modulation in the treatment of overactive bladder.

As used herein, "implanted" is taken to mean positioned at least partially within the subject's body. Partial implantation means that only part of the device is implanted—i.e. only part of the device is positioned within the subject's body, with other elements of the device external to the subject's body. Wholly implanted means that the entire of the device is positioned within the subject's body. For the avoidance of doubt, the apparatus being "wholly implanted" does not preclude additional elements, independent of the apparatus but in practice useful for its functioning (for example, a remote wireless charging unit or a remote wireless manual override unit), being independently formed and external to the subject's body. "Implantable" is taken to mean suitable for such implantation.

As used herein, "charge-balanced" in relation to a DC current is taken to mean that the positive or negative charge introduced into any system (e.g. a nerve) as a result of a DC current being applied is balanced by the introduction of the opposite charge in order to achieve overall (i.e. net) neutrality.

As shown herein, it has been identified that sleep apnoea can be treated by stimulation of the cervical sympathetic chain (CSC), superior cervical ganglion (SCG) and/or a postganglionic branch thereof. In addition, it has been identified that stimulation of the CSC, SCG and/or a postganglionic branch thereof is able to induce changes in skeletal muscle activity (specifically genioglossus and diaphragm muscle activity), unusually for sympathetic nerve stimulation. Malposition of the tongue (controlled by the genioglossus) is heavily involved in both CSA and OSA. Therefore, such changes in skeletal muscle activity provide further means of treating sleep apnoea by reducing or preventing the anatomical causes of sleep apnoea.

Further surprisingly, it has been identified that different aspects of sleep apnoea can be treated via differential unilateral stimulation and bilateral stimulation. That is, stimulation of the left CSC-SCG (or a component thereof) can induce improvements in one set of sleep apnoea symptoms (for example, reducing blood pressure), stimulation of the right CSC-SCG (or a component thereof) can induce improvements in another set of sleep apnoea symptoms (for example reducing respiratory rate/increasing tidal volume), and bilateral stimulation can induce improvements across both sets of sleep apnoea symptoms. Similarly, it is demonstrated herein that different physiological responses can be induced depending on the nature of the signal applied (for example, for an electrical signal, by varying the frequency and/or pulse duration). For example, different reductions in airway resistance and/or blood pressure can be induced depending on the nature of the signal applied.

Such differential effects will allow for targeted and specific treatment of whichever symptoms are being exhibited by a given subject, at a given time.

A neuromodulation device that stimulates the neural activity in a CSC, SCG and/or a postganglionic branch thereof of a subject will therefore provide an effective treatment for sleep apnoea.

Therefore, in accordance with one aspect of the invention there is provided an apparatus or system for increasing the neural activity of a CSC, SCG and/or postganglionic branch thereof of a subject, the apparatus comprising: a transducer configured to apply a signal to the nerve, optionally at least two such transducers; and a controller operably coupled to the transducer or transducers, the controller controlling the signal to be applied by each transducer, such that the signal modulates the neural activity of the nerve. In certain preferred embodiments, the signal stimulates localized sympathetic activity in the CSC, SCG and/or postganglionic neurons thereof. This stimulation in sympathetic activity produces a physiological response in the subject, for example one or more of: a decrease in blood pressure, a decrease in respiratory rate, an increase in tidal volume, a decrease in upper airway resistance, an increase in diaphragmatic muscle activity, an increase in genioglossus muscle activity, an increase in central respiratory drive. Thus, in a related aspect, the apparatus or system is provided for treating sleep apnoea in a subject, such as a patient experiencing or suffering from sleep apnoea.

In certain such embodiments, the signal applied by the one or more transducers is an electrical signal, an optical signal, an ultrasonic signal, or a thermal signal. In those embodiments in which the apparatus has at least two transducers, the signal which each of the transducers is configured to apply is independently selected from an electrical signal, an optical signal, an ultrasonic signal, and a thermal signal. That is, each transducer may be configured to apply a different signal. Alternatively, in certain embodiments each transducer is configured to apply the same signal.

In certain embodiments, each transducer may be comprised of one or more electrodes, one or more photon sources, one or more ultrasound transducers, one more sources of heat, or one or more other types of transducer arranged to put the signal into effect.

In certain embodiments, the signal applied is an electrical signal, for example a voltage or current. In certain such embodiments the signal applied comprises a direct current (DC) waveform, such as a charge balanced direct current waveform, or an alternating current (AC) waveform, or both a DC and an AC waveform.

In certain embodiments, the DC waveform or AC waveform may be a square, sinusoidal, triangular or complex waveform. The DC waveform may alternatively be a constant amplitude waveform.

It will be appreciated by the skilled person that the current amplitude of an applied electrical signal necessary to achieve the intended stimulation will depend upon the positioning of the electrode and the associated electrophysiological characteristics (e.g. impedance). It is within the ability of the skilled person to determine the appropriate current amplitude for achieving the intended stimulation in a given subject. For example, the skilled person is aware of methods suitable to monitor the neural activity profile induced by neuronal or nerve stimulation.

In certain embodiments, wherein the signal comprises an AC waveform and/or a DC waveform, each waveform has an independently selected frequency of 0.5-100 Hz, optionally 1-50 Hz, optionally of 1-25 Hz, optionally 1-10 Hz. In certain embodiments, the signal has a frequency of 1 Hz, 1.5 Hz, 2 Hz, 2.5 Hz, 3 Hz, 3.5 Hz, 4 Hz, 4.5 Hz, 5 Hz, 5.5 Hz, 6 Hz, 6.5 Hz, 7 Hz, 7.5 Hz, 8 Hz, 8.5 Hz, 9 Hz, 9.5 Hz, 10 Hz, 15 Hz, 20 Hz, 25 Hz, 30 Hz, 35 Hz, 40 Hz, 45 Hz, 50 Hz. In certain embodiments, the signal is an electrical signal having a frequency of 7.5 Hz. It will be appreciated by those of skill in the art that the lower and upper limits of such ranges can vary independently, such that the signal can have a frequency of at least 1 Hz, or at least 2.5 Hz, or at least 5 Hz, or at least 10 Hz, or at least 20 Hz, or at least 25 Hz, or at least 50 Hz, or at least 100 Hz. Such a signal can have a frequency less than 1 kHz, or 500 Hz, or 200 Hz, or 100 Hz, or 50 Hz or 20 Hz, or 10 Hz.

In certain embodiments, the signal is an electrical signal and is initiated at a first frequency and then altered to a second frequency, wherein (a) the first frequency is higher than the second frequency; or (b) the first frequency is lower than the second frequency.

In certain embodiments, the signal is an electrical signal having a voltage of 1-20V. In certain preferred embodiments, the signal has a voltage of 5-15V, optionally 10-15V. In certain preferred embodiments the voltage is selected from 5V, 10V and 15V. It will be appreciated by those of skill in the art that the lower and upper limits of such ranges can vary independently.

In certain embodiments, the signal is an electrical signal having a current of 0.1-5 mA, optionally 0.5-2 mA, optionally 0.75-1.5 mA, optionally 0.8-1 mA. In certain embodiments, the signal is an electrical signal having a current of at least 0.1 mA, at least 0.2 mA, at least 0.3 mA, at least 0.4 mA, at least 0.5 mA, at least 0.6 mA, at least 0.7 mA, at least 0.8 mA, at least 0.9 mA, at least 1.0 mA. It will be appreciated by those of skill in the art that the lower and upper limits of such ranges can vary independently, such that the signal can have a current of at least 0.1 mA, or at least 0.2 mA, or at least 0.3 mA, or at least 0.4 mA, or at least 0.5 mA, or at least 0.8 mA. Such a signal can have a current less than 5 mA, or 2 mA, or 1.5 mA, or 1 mA, or 0.8 mA. In certain preferred embodiments the signal has a current of less than 0.8 mA.

In certain embodiments the signal is an electrical signal having a pulse width of 0.05-5 ms, 0.1-5 ms, optionally 0.5-5 ms, optionally 1-3 ms, optionally 2 ms. In certain embodiments, the signal is an electrical signal having a pulse width of 0.2-5 ms. In certain embodiments, the signal has a pulse width of 0.1 ms, or 0.2 ms, or 0.5 ms, or 1 ms. It will be appreciated by those of skill in the art that the lower and upper limits of such ranges can vary independently, such that the signal can have a pulse duration of at least 0.05 ms, 0.1 ms, 0.2 ms, 0.5 ms, 1 ms or 2 ms. Such a signal can have a pulse duration less than 5 ms, 3 ms, 2 ms, 1 ms, 0.5 ms, 0.2 ms, or 0.1 ms.

In certain preferred embodiments, the signal comprises an AC waveform of 7.5 Hz 0.8 mA, or an AC waveform of 7.5 Hz 1 mA, or an AC waveform of 7.5 Hz 10V. In certain preferred embodiments, the signal comprises an AC waveform, has a current of at least 0.8 mA, has a pulse duration of 2 ms, and has a frequency selected from 2.5 Hz, 5 Hz, 7.5 Hz, 10 Hz, 20 Hz or 50 Hz. In certain preferred embodiments, the signal comprises an AC waveform, has a current of at least 0.5 mA, has a frequency of 5 Hz, and has a pulse duration selected from 0.1 ms, 0.2 ms, 0.5 ms, 1 ms or 2 ms.

In those embodiments in which the signal applied is an electrical signal, each transducer configured to apply the electrical signal is an electrode, for example a cuff or wire electrode. In certain such embodiments, all the transducers are electrodes configured to apply an electrical signal, optionally the same electrical signal.

In certain embodiments wherein the signal applied by the one or more transducers is a thermal signal, the signal reduces the temperature of the nerve (i.e. cools the nerve). In certain alternative embodiments, the signal increases the temperature of the nerve (i.e. heats the nerve). In certain embodiments, the signal both heats and cools the nerve.

In those embodiments in which the signal applied by the one or more transducers is a thermal signal, at least one of the one or more transducers is a transducer configured to apply a thermal signal. In certain such embodiments, all the transducers are configured to apply a thermal signal, optionally the same thermal signal.

In certain embodiments, one or more of the one or more transducers comprise a Peltier element configured to apply a thermal signal, optionally all of the one or more transducers comprise a Peltier element. In certain embodiments, one or more of the one or more transducers comprise a laser diode configured to apply a thermal signal, optionally all of the one or more transducers comprise a laser diode configured to apply a thermal signal. In certain embodiments, one or more of the one or more transducers comprise a electrically resistive element configured to apply a thermal signal, optionally all of the one or more transducers comprise a electrically resistive element configured to apply a thermal signal.

In certain embodiments the signal applied by the one or more transducers is a mechanical signal, optionally an ultrasonic signal. In certain alternative embodiments, the mechanical signal applied by the one or more transducers is a pressure signal.

In certain embodiments the signal applied by the one or more transducers is an electromagnetic signal, optionally an optical signal. In certain such embodiments, the one or more transducers comprise a laser and/or a light emitting diode configured to apply the optical signal.

In certain embodiments, the physiological response produced in the subject is one or more of: an decrease in systemic sympathetic tone, a decrease in duration of apnoeic episodes, a decrease in frequency of apnoeic episodes, a decrease in blood pressure (for example a decrease in mean arterial pressure), a decrease in respiratory rate, an increase in tidal volume, a decrease in upper airway resistance, an increase in diaphragmatic muscle activity (also referred to as diaphragmatic tone), an increase in genioglossus muscle activity (also referred to as genioglossus tone), an increase in central respiratory drive.

In certain embodiments, the apparatus further comprises a detector element to detect one or more physiological parameters in the subject. Such a detector element may be configured to detect the one or more physiological parameters. That is, in such embodiments each detector may detect more than one physiological parameter, for example all the detected physiological parameters. Alternatively, in such embodiments each of the one or more detector elements is configured to detect a separate parameter of the one or more physiological parameters detected.

In such embodiments, the controller is coupled to the detector element configured to detect one or more physiological parameters, and causes the transducer or transducers to apply the signal when the physiological parameter is detected to be meeting or exceeding a predefined threshold value.

In certain embodiments, the one or more detected physiological parameters are selected from: systemic sympathetic tone; diaphragmatic tone; genioglossus tone; blood pressure; respiratory rate; tidal volume; upper airway resistance.

In certain embodiments, the one or more detected physiological parameters comprise an action potential or pattern of action potentials in a nerve of the subject, wherein the action potential or pattern of action potentials is associated with sleep apnoea. In certain such embodiments, the nerve is part of the cervical sympathetic chain. In certain such embodiments, the nerve is a superior cervical ganglion or a postganglionic branch thereof.

It will be appreciated that any two or more of the indicated physiological parameters may be detected in parallel or consecutively. For example, in certain embodiments, the controller is coupled to a detector or detectors configured to detect the pattern of action potentials in a superior cervical ganglion and also to detect the blood pressure of the subject.

Application of the signal by an apparatus according to the invention causes an increase in neural activity in the nerve or nerves to which the signal is applied. That is, in such embodiments, application of the signal results in the neural activity in at least part of the nerve or nerves being increased compared to the baseline neural activity in that part of the nerve. Such an increase in activity could equally be across the whole nerve, in which case neural activity would be increased across the whole nerve or nerves. Therefore, in certain such embodiments, a result of applying the signal is an increase in neural activity in the nerve or nerves. In certain embodiments, a result of applying the signal is an increase in neural activity across the whole nerve or nerves.

In certain embodiments, neural activity may be further modulated as a result of applying the signal, for example resulting in an alteration to the pattern of action potentials in the nerve or nerves. In certain such embodiments, the neural activity is modulated such that the resultant pattern of action potentials in the nerve or nerves resembles the pattern of action potentials in the nerve or nerves observed in a healthy subject. Such modulation may comprise altering the neural activity in various other ways, for example increasing or inhibiting a particular part of the activity and stimulating new elements of activity, for example in particular intervals of time, in particular frequency bands, according to particular patterns and so forth.

In certain embodiments, the controller causes the signal to be applied intermittently. In certain such embodiments, the controller causes the signal to applied for a first time period, then stopped for a second time period, then reapplied for a third time period, then stopped for a fourth time period. In such an embodiment, the first, second, third and fourth periods run sequentially and consecutively. The series of first, second, third and fourth periods amounts to one application cycle. In certain such embodiments, multiple application cycles can run consecutively such that the signal is applied in phases, between which phases no signal is applied.

In certain embodiments, the application cycles are not immediately consecutive. In certain such embodiments the application cycles are separated by a period of 1-60 min, 5-30 min, 10-20 min, optionally 15 min.

In such embodiments, the duration of the first, second, third and fourth time periods is independently selected. That is, the duration of each time period may be the same or different to any of the other time periods. In certain such embodiments, the duration of each of the first, second, third and fourth time periods is any time from 5 seconds (5 s) to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is independently selected from: 0.8 s-2 min, 0.8 s-30 s, 0.8 s-10 s, 0.8 s-5 s, 0.8-2 s, 10 s-2 min, 30 s-2 min, 30 s-1 min, optionally 30 s. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h. In certain embodiments, the first and third periods are not 3 minutes and the second and fourth periods are not 10 minutes.

In certain embodiments, immediately consecutive application cycles are applied for an operative period—that is, an operative period is a period over which consecutive application cycles are in operation. In such embodiments, the operative period is immediately followed by an inoperative period. In certain embodiments, the operative and inoperative period have a duration independently selected from 1-60 min, 5-30 min, 10-20 min, optionally 15 min. In certain embodiments, the operative and inoperative period have a duration independently selected from 1-24 h, 1-12 h, 1-6 h, optionally 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h.

In certain embodiments wherein the controller causes the signal to be applied intermittently, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

In certain embodiments wherein the controller causes the signal to be applied intermittently, the signal is applied only when the subject is in a specific physiological state. For example, in certain embodiments, the signal may be applied only when the subject is asleep, and/or only when the subject is undergoing an apnoeic episode.

In certain such embodiments, the apparatus further comprises a communication, or input, element via which the status of the subject (e.g. that they are going to sleep) can be indicated by the subject or a physician. In alternative embodiments, the apparatus further comprises a detector configured to detect the status of the subject, wherein the signal is applied only when the detector detects that the subject is in the specific state.

In certain embodiments, the detector detects that the subject or patient is undergoing an apnoeic episode characterised by one or more physiological parameters being at or beyond the threshold value for each parameter. In response, the controller causes a signal to be applied either bilaterally, unilaterally (right) or unilaterally (left), depending on which parameters characterise the apnoeic episode. For example, if the apnoeic episode is characterised predominantly by a detected increase in blood pressure, the controller might cause the signal to be applied unilaterally to the left CSC-SCG (or a component thereof). By way of further example, if the apnoeic episode is characterised predominantly by a detected increase in respiratory rate/decrease in tidal volume, the controller might cause the signal to be applied unilaterally to the right CSC-SCG (or a component thereof). By way of yet further example, if the apnoeic episode is characterised predominantly by an increase in blood pressure and a detected increase in respiratory rate/decrease in tidal volume, the controller might cause the signal to be applied bilaterally in order to treat all characterising parameters of the apnoeic episode.

In certain alternative embodiments, the controller causes the signal to be permanently applied. That is, once begun, the signal is continuously applied to the nerve or nerves. It will be appreciated that in embodiments wherein the signal is a series of pulses, gaps between pulses do not mean the signal is not continuously applied.

In certain embodiments of the apparatus, the modulation in neural activity caused by the application of the signal is temporary. That is, upon cessation of the signal, neural activity in the nerve or nerves returns substantially towards baseline neural activity within 1-60 seconds, or within 1-60 minutes, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e. prior to stimulation.

In certain alternative embodiments, the increase in neural activity caused by the application of the signal or signals is substantially persistent. That is, upon cessation of the signal, neural activity in the nerve or nerves remains substantially the same as when the signal was being applied—i.e. the neural activity during and following stimulation is substantially the same.

In certain embodiments, the increase in neural activity caused by the application of the signal is partially corrective, preferably substantially corrective. That is, upon cessation of the signal, neural activity in the nerve or nerves more closely resembles the pattern of action potentials in the nerve(s) observed in a healthy subject than prior to stimulation, preferably substantially fully resembles the pattern of action potentials in the nerve(s) observed in a healthy subject. For example, application of the signal may result in an increase in neural activity, and upon cessation of the signal, the pattern of action potentials in the nerve or nerves resembles the pattern of action potentials observed in a healthy individual. It is hypothesised that such a corrective effect is the result of a positive feedback loop—that is, the underlying predisposition to sleep apnoea is treated as result of the stimulation caused by application of the signal.

In certain embodiments, the apparatus is suitable for at least partial implantation into the subject. In certain such embodiments, the apparatus is suitable to be fully implanted in the subject. For the avoidance of doubt, the apparatus being "wholly implanted" does not preclude additional elements, independent of the apparatus but in practice useful for its functioning (for example, a remote wireless charging unit or a remote wireless manual override unit), being independently formed and external to the subject's body.

In certain embodiments, the apparatus further comprises one or more power supply elements, for example a battery, and/or one or more communication elements.

In another aspect, the invention provides a method of treating sleep apnoea (OSA and/or CSA), the method comprising implanting an apparatus according to the first aspect, positioning at least one transducer of the apparatus in signalling contact with a CSC, SCG and/or postganglionic branch thereof of a subject, and activating the apparatus. In such embodiments, the transducer is in signalling contact with the nerve when it is positioned such that the signal can be effectively applied to the nerve. The apparatus is activated when the apparatus is in an operating state such that the signal will be applied as determined by the controller.

In certain such embodiments, a first transducer is positioned in signalling contact with a left CSC, SCG and/or postganglionic branch of said subject to stimulate the neural activity of said left CSC, SCG and/or postganglionic branch in the subject, and a second transducer is positioned in signalling contact with a right CSC, SCG and/or postganglionic branch of said subject to stimulate the neural activity of said right CSC, SCG and/or postganglionic branch in the subject. In certain such embodiments, the first and second transducers are part of one apparatus according to the first aspect. In alternative such embodiments, the first and second transducers are part of separate apparatuses according to the first aspect.

Implementation of all aspects of the invention (as discussed both above and below) will be further appreciated by reference to FIGS. 3A-3C.

Figure 3A:
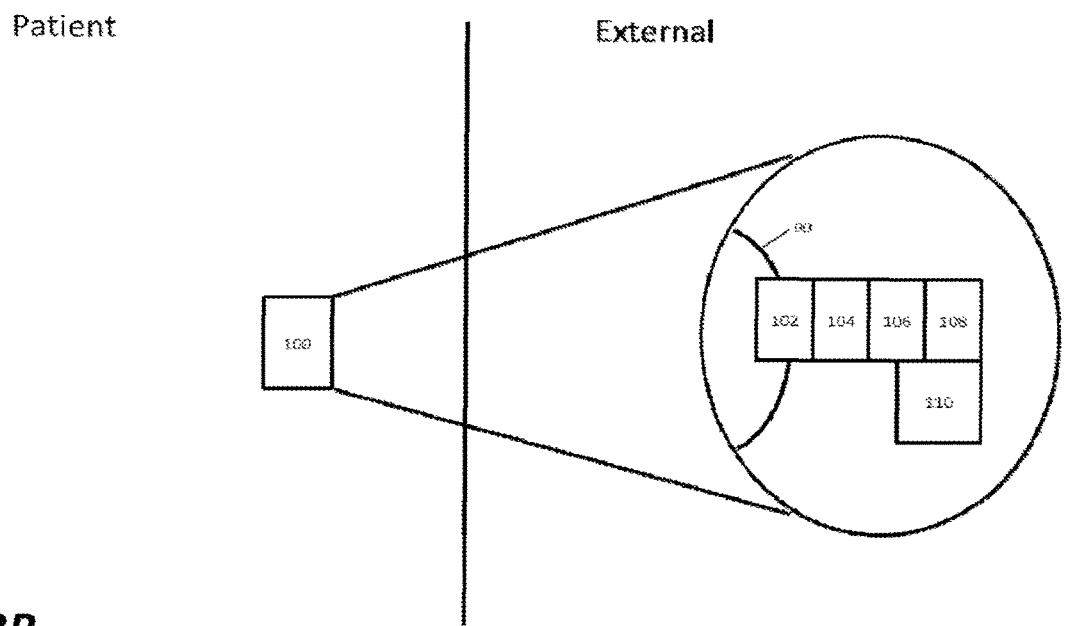
FIGS. 3A-3C: Schematic drawings showing how apparatuses, devices and methods according to the invention can be put into effect.
Figure 3B:
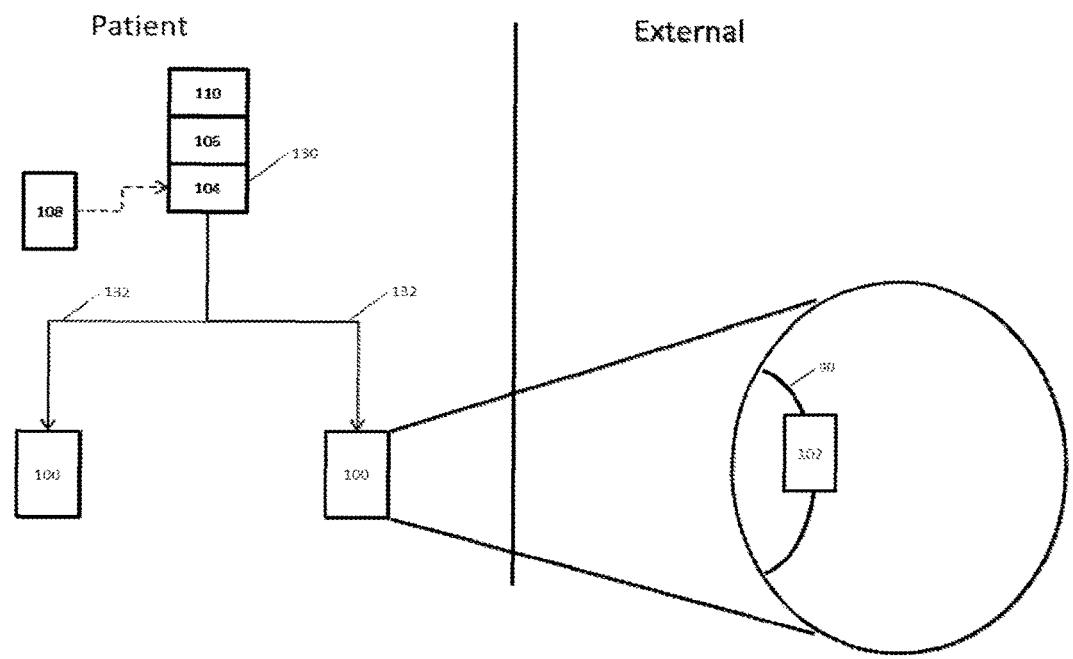
Figure 3C:
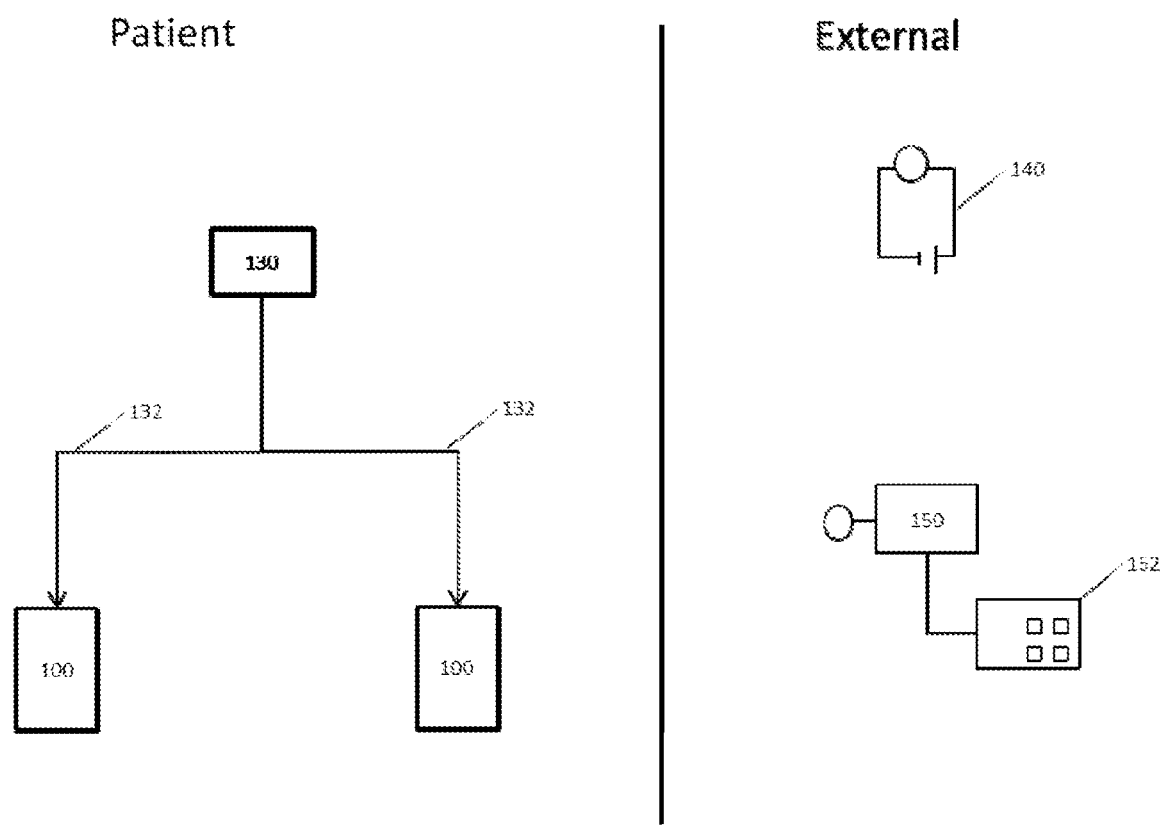

FIGS. 3A-3C show how the invention may be put into effect using one or more neuromodulation devices which are implanted in, located on, or otherwise disposed with respect to a subject in order to carry out any of the various methods described herein. In this way, one or more neuromodulation apparatuses can be used to treat sleep apnoea in a subject, by stimulating neural activity in a CSC, SCG and/or postganglionic branch thereof of the subject.

In each of the FIGS. 3B-3C a separate neuromodulation device 100 is provided in respect of each of the left and right CSC-SCG complex, although as discussed herein a device could be provided or used in respect of only one of the CSC-SCG complex. As described herein, the device could be provided or used in relation to any one or more elements of the CSC-SCG complex (e.g. the CSC, SCG and/or a postganglionic branch thereof). Each such neuromodulation device may be fully or partially implanted in the subject, or otherwise located, so as to provide neuromodulation of the respective nerve or nerves. Each of the left and right neuromodulation devices 100 may operate independently, or may operate in communication with each other.

FIG. 3A also shows schematically components of an implanted neuromodulation device 100, in which the device comprises several elements, components or functions grouped together in a single unit and implanted in the subject. A first such element is a transducer 102 which is shown in proximity to a CSC, SCG or postganglionic neuron thereof 90 of the subject. The transducer 102 may be operated by a controller element 104. The device may comprise one or more further elements such as a communication element 106, a detector element 108, a power supply element 110 and so forth.

Each neuromodulation device 100 may carry out the required neuromodulation independently, or in response to one or more control signals. Such a control signal may be provided by the controller element 104 according to an algorithm, in response to output of one or more detector elements 108, and/or in response to communications from one or more external sources received using the communications element. As discussed herein, the detector element(s) could be responsive to a variety of different physiological parameters, as described below.

FIG. 3B illustrates some ways in which the apparatus of FIG. 3A may be differently distributed. For example, in FIG. 3B the neuromodulation devices 100 comprise transducers 102 implanted proximally to a CSC, SCG or postganglionic branch 90, but other elements such as a controller element 104, a communication element 106 and a power supply 110 are implemented in a separate control unit 130 which may also be implanted in, or carried by the subject. The control unit 130 then controls the transducers in both of the neuromodulation devices via connections 132 which may for example comprise electrical wires and/or optical fibres for delivering signals and/or power to the transducers.

In the arrangement of FIG. 3B one or more detector elements 108 are located separately from the control unit, although one or more such detector elements could also or instead be located within the control unit 130 and/or in one or both of the neuromodulation devices 100. The detector elements may be used to detect one or more physiological parameters of the subject, and the controller element or control unit then causes the transducers to apply the signal in response to the detected parameter(s), for example only when a detected physiological parameter meets or exceeds a predefined threshold value. Physiological parameters which could be detected for such purposes include one or more of: sympathetic tone; diaphragmatic tone; genioglossus tone; blood pressure; respiratory rate; tidal volume; upper airway resistance; central respiratory drive. Similarly, a detected physiological parameter could be an action potential or pattern of action potentials in a nerve of the subject, for example a CSC, SCG and/or postganglionic branch, wherein the action potential or pattern of action potentials is associated with sleep apnoea.

As already described, in arrangements such as those of FIG. 3B or 3C, detector elements may be used to detect physiological parameters that characterise a particular apnoeic episode. In response, the controller element or control unit can cause the transducers to apply the signal bilaterally, unilaterally (left) or unilaterally (right), depending on the parameters characterising the particular apnoeic episode. For example, if the apnoeic episode is characterised predominantly by a detected increase in blood pressure, the controller element might cause the signal to be applied unilaterally to the left CSC-SCG (or a component thereof). By way of further example, if the apnoeic episode is characterised predominantly by a detected increase in respiratory rate/decrease in tidal volume, the controller element might cause the signal to be applied unilaterally to the right CSC-SCG (or a component thereof). By way of yet further example, if the apnoeic episode is characterised predominantly by an increase in blood pressure and a detected increase in respiratory rate/decrease in tidal volume, the controller element might cause the signal to be applied bilaterally in order to treat all characterising parameters of the apnoeic episode.

A variety of other ways in which the various functional elements could be located and grouped into the neuromodulation devices, a control unit 130 and elsewhere are of course possible. For example, one or more sensors of FIG. 3B could be used in the arrangement of FIG. 3A or 3C or other arrangements.

FIG. 3C illustrates some ways in which some functionality of the apparatus of FIG. 3A or 3B is provided not implanted in the subject. For example, in FIG. 3C an external power supply 140 is provided which can provide power to implanted elements of the apparatus in ways familiar to the skilled person, and an external controller 150 provides part or all of the functionality of the controller element 104, and/or provides other aspects of control of the apparatus, and/or provides data readout from the apparatus, and/or provides a data input facility 152. The data input facility could be used by a subject or other operator in various ways, for example to input data relating to the status of the subject (e.g. if they are about to go to sleep).

Each neuromodulation device may be adapted to carry out the neuromodulation required using one or more physical modes of operation which typically involve applying a signal to a CSC, SCG and/or postganglionic branch, such a signal typically involving a transfer of energy to (or from) the nerve(s). As already discussed, such modes may comprise stimulating neural activity in the nerve or nerves using an electrical signal, an optical signal, an ultrasound or other mechanical signal, a thermal signal, a magnetic or electromagnetic signal, or some other use of energy to carry out the required stimulation. To this end, the transducer 102 illustrated in FIG. 3A could be comprised of one or more electrodes, one or more photon sources, one or more ultrasound transducers, one more sources of heat, or one or more other types of transducer arranged to put the required neuromodulation into effect.

In certain embodiments, the signal applied is an electrical signal, for example a voltage or current. In certain such embodiments the signal applied comprises a direct current (DC) waveform, such as a charge balanced direct current waveform, or an alternating current (AC) waveform, or both a DC and an AC waveform.

In certain embodiments, the DC waveform or AC waveform may be a square, sinusoidal, triangular or complex waveform. The DC waveform may alternatively be a constant amplitude waveform.

It will be appreciated by the skilled person that the current/voltage amplitude of an applied electrical signal necessary to achieve the intended stimulation will depend upon the positioning of the electrode and the associated electrophysiological characteristics (e.g. impedance). It is within the ability of the skilled person to determine the appropriate current amplitude for achieving the intended stimulation in a given subject. For example, the skilled person is aware of methods suitable to monitor the neural activity profile induced by neuronal or nerve stimulation.

In certain embodiments, wherein the signal comprises an AC waveform and/or a DC waveform, each waveform has an independently selected frequency of 0.5-100 Hz, optionally 1-50 Hz, optionally of 1-25 Hz, optionally 1-10 Hz. In certain embodiments, the signal has a frequency of 1 Hz, 1.5 Hz, 2 Hz, 2.5 Hz, 3 Hz, 3.5 Hz, 4 Hz, 4.5 Hz, 5 Hz, 5.5 Hz, 6 Hz, 6.5 Hz, 7 Hz, 7.5 Hz, 8 Hz, 8.5 Hz, 9 Hz, 9.5 Hz, 10 Hz, 15 Hz, 20 Hz, 25 Hz, 30 Hz, 35 Hz, 40 Hz, 45 Hz, 50 Hz. In certain embodiments, the signal is an electrical signal having a frequency of 7.5 Hz. It will be appreciated by those of skill in the art that the lower and upper limits of such ranges can vary independently, such that the signal can have a frequency of at least 1 Hz, or at least 2.5 Hz, or at least 5 Hz, or at least 10 Hz, or at least 20 Hz, or at least 25 Hz, or at least 50 Hz, or at least 100 Hz. Such a signal can have a frequency less than 1 kHz, or 500 Hz, or 200 Hz, or 100 Hz, or 50 Hz or 20 Hz, or 10 Hz.

In certain embodiments, the signal is an electrical signal and is initiated at a first frequency and then altered to a second frequency, wherein (a) the first frequency is higher than the second frequency; or (b) the first frequency is lower than the second frequency.

In certain embodiments, the signal is an electrical signal having a voltage of 1-20V. In certain preferred embodiments, the signal has a voltage of 5-15V, optionally 10-15V. In certain preferred embodiments the voltage is selected from 5V, 10V and 15V.

In certain embodiments, the signal is an electrical signal having a current of 0.1-5 mA, optionally 0.5-2 mA, optionally 0.75-1.5 mA, optionally 0.8-1 mA. In certain embodiments, the signal is an electrical signal having a current of at least 0.1 mA, at least 0.2 mA, at least 0.3 mA, at least 0.4 mA, at least 0.5 mA, at least 0.6 mA, at least 0.7 mA, at least 0.8 mA, at least 0.9 mA, at least 1.0 mA. It will be appreciated by those of skill in the art that the lower and upper limits of such ranges can vary independently, such that the signal can have a current of at least 0.1 mA, or at least 0.2 mA, or at least 0.3 mA, or at least 0.4 mA, or at least 0.5 mA, or at least 0.8 mA. Such a signal can have a current less than 5 mA, or 2 mA, or 1.5 mA, or 1 mA, or 0.8 mA. In certain preferred embodiments the signal has a current of less than 0.8 mA.

In certain embodiments the signal is an electrical signal having a pulse width of 0.1-5 ms, optionally 0.5-5 ms, optionally 1-3 ms, optionally 2 ms. In certain embodiments, the signal is an electrical signal having a pulse width of 0.2-5 ms. In certain embodiments, the signal has a pulse width of 0.1 ms, or 0.2 ms, or 0.5 ms, or 1 ms. It will be appreciated by those of skill in the art that the lower and upper limits of such ranges can vary independently, such that the signal can have a pulse duration of at least 0.05 ms, 0.1 ms, 0.2 ms, 0.5 ms, 1 ms or 2 ms. Such a signal can have a pulse duration less than 5 ms, 3 ms, 2 ms, 1 ms, 0.5 ms, 0.2 ms, or 0.1 ms.

In certain preferred embodiments, the signal comprises an AC waveform of 7.5 Hz 0.8 mA, or an AC waveform of 7.5 Hz 1 mA, or an AC waveform of 7.5 Hz 10V. In certain preferred embodiments, the signal comprises an AC waveform, has a current of at least 0.8 mA, has a pulse duration of 2 ms, and has a frequency selected from 2.5 Hz, 5 Hz, 7.5 Hz, 10 Hz, 20 Hz or 50 Hz. In certain preferred embodiments, the signal comprises an AC waveform, has a current of at least 0.5 mA, has a frequency of 5 Hz, and has a pulse duration selected from 0.1 ms, 0.2 ms, 0.5 ms, 1 ms or 2 ms.

In those embodiments in which the signal applied is an electrical signal, each transducer configured to apply the electrical signal is an electrode, for example a cuff or wire electrode. In certain such embodiments, all the transducers are electrodes configured to apply an electrical signal, optionally the same electrical signal.

In a third aspect, the invention provides a method of treating sleep apnoea, for example OSA and/or CSA, in a subject, the method comprising applying a signal to a part or all of a CSC, SCG and/or a postganglionic branch thereof of said subject to stimulate the neural activity of said CSC, SCG and/or postganglionic branch thereof in the subject.

In certain embodiments, the signal is applied by a neuromodulation device comprising one or more transducers configured to apply the signal. In certain preferred embodiments the neuromodulation device is at least partially implanted in the subject. In certain preferred embodiments, the neuromodulation device is wholly implanted in the subject. For the avoidance of doubt, the apparatus being "wholly implanted" does not preclude additional elements, independent of the apparatus but in practice useful for its functioning (for example, a remote wireless charging unit or a remote wireless manual override unit), being independently formed and external to the subject's body.

In certain embodiments, the treatment of sleep apnoea is treatment of CSA or treatment of OSA. In certain embodiments, the treatment is characterised by the subject exhibiting less frequent and/or less severe episodes of sleep apnoea than before treatment. In certain embodiments, treatment may be characterised by amelioration of an ongoing apnoeic episode.

In certain embodiments, treatment of sleep apnoea is indicated by an improvement in a measurable physiological parameter, for example one or more of: a decrease in duration of apnoeic episodes, a decrease in frequency of apnoeic episodes, a decrease in blood pressure (for example a decrease in mean arterial pressure), a decrease in respiratory rate, an increase in tidal volume, a decrease in upper airway resistance, an increase in diaphragmatic muscle activity (also referred to as diaphragmatic tone), an increase in genioglossus muscle activity (also referred to as genioglossus tone), an increase in central respiratory drive. Suitable methods for determining the value for any given parameter would be appreciated by the skilled person and examples have been described above.

It will be appreciated that treatment of sleep apnoea, for example OSA and/or CSA, may include one or more or all of the above characteristics. That is, treatment of sleep apnoea according to the method may be characterised by reduced blood pressure, and less frequent apnoeic episodes, with any episode also being less severe than before treatment.

In certain embodiments, treatment of the condition is indicated by an improvement in the profile of neural activity in the nerve or nerves to which the signal is applied. That is, treatment of the condition is indicated by the neural activity in the nerve(s) approaching the neural activity in a healthy individual—i.e. the pattern of action potentials in the nerve more closely resembling that exhibited by a healthy individual than before the intervention.

Stimulation of neural activity as a result of applying the signal is an increase in neural activity in the nerve or nerves. That is, in such embodiments, application of the signal results in the neural activity in at least part of the nerve(s) being increased compared to the baseline neural activity in that part of the nerve.

Neural activity may also be modulated as a result of applying the signal such that there is an alteration to the pattern of action potentials in nerve or nerves to which a signal is applied. In certain such embodiments, the neural activity is modulated such that the resultant pattern of action potentials in the nerve or nerves resembles the pattern of action potentials in the nerve(s) observed in a healthy subject.

In certain embodiments, the signal is applied intermittently. In certain such embodiments, the signal is applied for a first time period, then stopped for a second time period, then reapplied for a third time period, then stopped for a fourth time period. In such an embodiment, the first, second, third and fourth periods run sequentially and consecutively. The series of first, second, third and fourth periods amounts to one application cycle. In certain such embodiments, multiple application cycles can run consecutively such that the signal is applied in phases, between which phases no signal is applied.

In certain embodiments, the application cycles are not immediately consecutive. In certain such embodiments the application cycles are separated by a period of 1-60 min, 5-30 min, 10-20 min, optionally 15 min.

In such embodiments, the duration of the first, second, third and fourth time periods is independently selected. That is, the duration of each time period may be the same or different to any of the other time periods. In certain embodiments, the first, second, third and fourth periods are independently selected from: 0.8 s-2 min, 0.8 s-30 s, 0.8 s-10 s, 0.8 s-5 s, 0.8-2 s, 10 s-2 min, 30 s-2 min, 30 s-1 min, optionally 30 s. In certain embodiments, the duration of each of the first, second, third and fourth time periods is any time from 5 seconds (5 s) to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is independently selected from 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h. In certain embodiments, the first and third periods are not 3 minutes and the second and fourth periods are not 10 minutes.

In certain embodiments, immediately consecutive application cycles are applied for an operative period—that is, an operative period is a period over which consecutive application cycles are in operation. In such embodiments, the operative period is immediately followed by an inoperative period. In certain embodiments, the operative and inoperative period have a duration independently selected from 1-60 min, 5-30 min, 10-20 min, optionally 15 min. In certain embodiments, the operative and inoperative period have a duration independently selected from 1-24 h, 1-12 h, 1-6 h, optionally 1 h, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h.

In certain embodiments wherein the signal is applied intermittently, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain embodiments, the signal is applied continuously for the specified amount of time. In certain alternative such embodiments, the signal may be applied discontinuously across the day, provided the total time of application amounts to the specified time.

In certain embodiments wherein the controller causes the signal to be applied intermittently, the signal is applied only when the subject is in a specific physiological state. For example, in certain embodiments, the signal may be applied only when the subject is asleep, and/or only when the subject is undergoing an apnoeic episode.

In certain such embodiments, the apparatus further comprises a communication, or input, element via which the status of the subject (e.g. that they are going to sleep) can be indicated by the subject or a physician. In alternative embodiments, the apparatus further comprises a detector configured to detect the status of the subject, wherein the signal is applied only when the detector detects that the subject is in the specific state.

In certain embodiments, the one or more detected physiological parameters are selected from: sympathetic tone; diaphragmatic tone; genioglossus tone; blood pressure; respiratory rate; tidal volume; upper airway resistance, central respiratory drive.

In certain embodiments, the one or more detected physiological parameters comprise an action potential or pattern of action potentials in a nerve of the subject, wherein the action potential or pattern of action potentials is associated with sleep apnoea. In certain such embodiments, the nerve is part of the cervical sympathetic chain. In certain such embodiments, the nerve is a superior cervical ganglion.

It will be appreciated that any two or more of the indicated physiological parameters may be detected in parallel or consecutively. For example, in certain embodiments, the controller is coupled to a detector or detectors configured to detect the pattern of action potentials in a superior cervical ganglion and also to detect the blood pressure of the subject.

In certain embodiments, the detector detects that the subject or patient is undergoing an apnoeic episode characterised by one or more physiological parameters being at or beyond the threshold value for each parameter. In response, the controller causes a signal to be applied either bilaterally, unilaterally (right) or unilaterally (left), depending on which parameters characterise the apnoeic episode. For example, if the apnoeic episode is characterised predominantly by a detected increase in blood pressure, the controller might cause the signal to be applied unilaterally to the left CSC, SCG and/or postganglionic branch thereof. By way of further example, if the apnoeic episode is characterised predominantly by a detected increase in respiratory rate and/or decrease in tidal volume, the controller might cause the signal to be applied unilaterally to the right CSC, SCG and/or postganglionic branch thereof. By way of yet further example, if the apnoeic episode is characterised predominantly by an increase in blood pressure and a detected increase in respiratory rate and/or decrease in tidal volume, the controller might cause the signal to be applied bilaterally in order to treat all characterising parameters of the apnoeic episode.

In certain embodiments, the signal is permanently applied. That is, once begun, the signal is continuously applied to the nerve or nerves. It will be appreciated that in embodiments wherein the signal is a series of pulses, gaps between pulses do not mean the signal is not continuously applied.

In certain embodiments of the methods, the stimulation in neural activity caused by the application of the signal is temporary. That is, upon cessation of the signal, neural activity in the nerve or nerves returns substantially towards baseline neural activity within 1-60 seconds, or within 1-60 minutes, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e. prior to modulation.

In certain alternative embodiments, the stimulation in neural activity caused by the application of the signal is substantially persistent. That is, upon cessation of the signal, neural activity in the nerve or nerves remains substantially the same as when the signal was being applied—i.e. the neural activity during and following stimulation is substantially the same.

In certain embodiments, the stimulation in neural activity caused by the application of the signal is partially corrective, preferably substantially corrective. That is, upon cessation of the signal, neural activity in the nerve or nerves more closely resembles the pattern of action potentials observed in a healthy subject than prior to modulation, preferably substantially fully resembles the pattern of action potentials observed in a healthy subject. In such embodiments, upon cessation of the signal, the pattern of action potentials in the nerve or nerves resembles the pattern of action potentials observed in a healthy subject. It is hypothesised that such a corrective effect is the result of a positive feedback loop.

In certain such embodiments, once first applied, the signal may be applied intermittently or permanently, as described in the embodiments above.

As is known by the skilled person, mammals have a left and a right CSC-SCG complex. Therefore, in certain embodiments, the signal is applied bilaterally. That is, in such embodiments, the signal is applied to a CSC, SCG and/or postganglionic branch thereof on both the left and right side of the subject such that the neural activity is stimulated in the nerves to which the signal is applied—i.e. the modulation is bilateral. In such embodiments, the signal applied to each nerve, and therefore the extent of stimulation is independently selected from that applied to the other nerve or nerves. In certain embodiments the signal applied to the right nerve or nerves is the same as the signal applied to the left nerve or nerves. In certain alternative embodiments the signal applied to the right nerve or nerves is different to the signal applied to the left nerve or nerves.

In certain embodiments wherein the modulation is bilateral, each signal is applied by a neuromodulation device comprising one or more transducers for applying the signal. In certain such embodiments, all signals are applied by the same neuromodulation device, that device have at least two transducers, one to apply the signal to the left nerve(s) and one to apply the signal to the right nerve(s). In certain alternative embodiments, each signal is applied by a separate neuromodulation device.

In certain embodiments of the methods according to the invention, the signal applied is an electrical signal, an electromagnetic signal (optionally an optical signal), a mechanical (optionally ultrasonic) signal, a thermal signal, a magnetic signal or any other type of signal.

In certain such embodiments in which more than one signal may be applied, for example when the modulation is bilateral, each signal may be independently selected from an electrical signal, an optical signal, an ultrasonic signal, and a thermal signal. In those such embodiments in which two signals are applied by one modulation device, the two signals may be the same type of signal or may be different types of signal independently selected from an electrical signal, an optical signal, an ultrasonic signal, and a thermal signal. In those embodiments in which two signals are applied, each by a separate neuromodulation device, the two signals may be the same type of signal or may be different types of signal independently selected from an electrical signal, an optical signal, an ultrasonic signal, and a thermal signal.

In certain embodiments in which the signal is applied by a neuromodulation device comprising at least one transducer, the transducer may be comprised of one or more electrodes, one or more photon sources, one or more ultrasound transducers, one more sources of heat, or one or more other types of transducer arranged to put the signal into effect.

In certain embodiments, the signal is an electrical signal, for example a voltage or current. In certain such embodiments the signal comprises a direct current (DC) waveform, such as a charge balanced DC waveform, or an alternating current (AC) waveform, or both a DC and an AC waveform.

In certain embodiments, the signal applied is an electrical signal, for example a voltage or current. In certain such embodiments the signal applied comprises a direct current (DC) waveform, such as a charge balanced direct current waveform, or an alternating current (AC) waveform, or both a DC and an AC waveform.

In certain embodiments, the DC waveform or AC waveform may be a square, sinusoidal, triangular or complex waveform. The DC waveform may alternatively be a constant amplitude waveform.

It will be appreciated by the skilled person that the current/voltage amplitude of an applied electrical signal necessary to achieve the intended stimulation will depend upon the positioning of the electrode and the associated electrophysiological characteristics (e.g. impedance). It is within the ability of the skilled person to determine the appropriate current amplitude for achieving the intended stimulation in a given subject. For example, the skilled person is aware of methods suitable to monitor the neural activity profile induced by neuronal or nerve stimulation.

In certain embodiments, wherein the signal comprises an AC waveform and/or a DC waveform, each waveform has an independently selected frequency of 0.5-100 Hz, optionally 1-50 Hz, optionally of 1-25 Hz, optionally 1-10 Hz. In certain embodiments, the signal has a frequency of 1 Hz, 1.5 Hz, 2 Hz, 2.5 Hz, 3 Hz, 3.5 Hz, 4 Hz, 4.5 Hz, 5 Hz, 5.5 Hz, 6 Hz, 6.5 Hz, 7 Hz, 7.5 Hz, 8 Hz, 8.5 Hz, 9 Hz, 9.5 Hz, 10 Hz, 15 Hz, 20 Hz, 25 Hz, 30 Hz, 35 Hz, 40 Hz, 45 Hz, 50 Hz. In certain embodiments, the signal is an electrical signal having a frequency of 5 Hz, 7.5 Hz, 10 Hz, or 20 Hz. It will be appreciated by those of skill in the art that the lower and upper limits of such ranges can vary independently, such that the signal can have a frequency of at least 1 Hz, or at least 2.5 Hz, or at least 5 Hz, or at least 10 Hz, or at least 20 Hz, or at least 25 Hz, or at least 50 Hz, or at least 100 Hz. Such a signal can have a frequency less than 1 kHz, or 500 Hz, or 200 Hz, or 100 Hz, or 50 Hz or 20 Hz, or 10 Hz.

In certain embodiments, the signal is an electrical signal having a voltage of 1-20V. In certain preferred embodiments, the signal has a voltage of 5-15V, optionally 10-15V. In certain preferred embodiments the voltage is selected from 5V, 10V and 15V.

In certain embodiments, the signal is an electrical signal having a current of 0.1-5 mA, optionally 0.5-2 mA, optionally 0.75-1.5 mA, optionally 0.8-1 mA. In certain embodiments, the signal is an electrical signal having a current of at least 0.1 mA, at least 0.2 mA, at least 0.3 mA, at least 0.4 mA, at least 0.5 mA, at least 0.6 mA, at least 0.7 mA, at least 0.8 mA, at least 0.9 mA, at least 1.0 mA. It will be appreciated by those of skill in the art that the lower and upper limits of such ranges can vary independently, such that the signal can have a current of at least 0.1 mA, or at least 0.2 mA, or at least 0.3 mA, or at least 0.4 mA, or at least 0.5 mA, or at least 0.8 mA. Such a signal can have a current less than 5 mA, or 2 mA, or 1.5 mA, or 1 mA, or 0.8 mA. In certain preferred embodiments the signal has a current of less than 0.8 mA.

In certain embodiments the signal is an electrical signal having a pulse width of 0.1-5 ms, optionally 0.5-5 ms, optionally 1-3 ms, optionally 2 ms. In certain embodiments, the signal is an electrical signal having a pulse width of 0.2-5 ms. In certain embodiments, the signal has a pulse width of 0.1 ms, or 0.2 ms, or 0.5 ms, or 1 ms. It will be appreciated by those of skill in the art that the lower and upper limits of such ranges can vary independently, such that the signal can have a pulse duration of at least 0.05 ms, 0.1 ms, 0.2 ms, 0.5 ms, 1 ms or 2 ms. Such a signal can have a pulse duration less than 5 ms, 3 ms, 2 ms, 1 ms, 0.5 ms, 0.2 ms, or 0.1 ms.

In certain preferred embodiments, the signal comprises an AC waveform of 7.5 Hz 0.8 mA, or an AC waveform of 7.5 Hz 1 mA, or an AC waveform of 7.5 Hz 10V. In certain preferred embodiments, the signal comprises an AC waveform, has a current of at least 0.8 mA, has a pulse duration of 2 ms, and has a frequency selected from 2.5 Hz, 5 Hz, 7.5 Hz, 10 Hz, 20 Hz or 50 Hz. In certain preferred embodiments, the signal comprises an AC waveform, has a current of at least 0.5 mA, has a frequency of 5 Hz, and has a pulse duration selected from 0.1 ms, 0.2 ms, 0.5 ms, 1 ms or 2 ms.

In those embodiments in which the signal applied is an electrical signal, each transducer configured to apply the electrical signal is an electrode, for example a cuff or wire electrode. In certain such embodiments, all the transducers are electrodes configured to apply an electrical signal, optionally the same electrical signal.

In a fourth aspect, the invention provides a neuromodulatory electrical waveform for use in treating sleep apnoea in a subject, wherein the waveform is an alternating current (AC) or direct current (DC) waveform having a frequency of 1-50 Hz, such that, when applied to a CSC, SCG and/or postganglionic branch the waveform stimulates neural signalling in the nerve. In certain embodiments, the waveform, when applied to the nerve, relieves or prevents sleep apnoea.

In a fifth aspect, the invention provides use of a neuromodulation device for treating sleep apnoea in a subject by stimulating neural activity in a CSC, SCG and/or postganglionic branch thereof of the subject. In certain embodiments, the device is an apparatus or system as described herein. In certain embodiments, the device delivers a signal to a CSC, SCG and/or postganglionic branch thereof of the subject.

In a preferred embodiment of all aspects of the invention, the subject or patient is a mammal, more preferably a human.

In a preferred embodiment of all aspects of the invention, the signal or signals is/are applied substantially exclusively to the nerves or nerve fibres specified, and not to other nerves or nerve fibres.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

EXAMPLES

The present inventors have developed a therapeutic method and apparatus for stimulating the cervical sympathetic chain (CSC), e.g., unilaterally or bilaterally, including, for example, the superior cervical ganglion (SCG) to treat sleep apnoea. This is illustrated by the following examples.

Example 1 Results

Bilateral CSC/SCG Stimulation Reduces Apnoeas and Disordered Breathing in Conscious Rats Hypoxic-hypercapnic (H—H) gas challenge is a recognised model for inducing and analysing disordered breathing, including apnoeas. Conscious Sprague-Dawley rats were exposed to H—H gas challenge and bilateral stimulation of CSC (or sham) was applied.

Figure 4A:
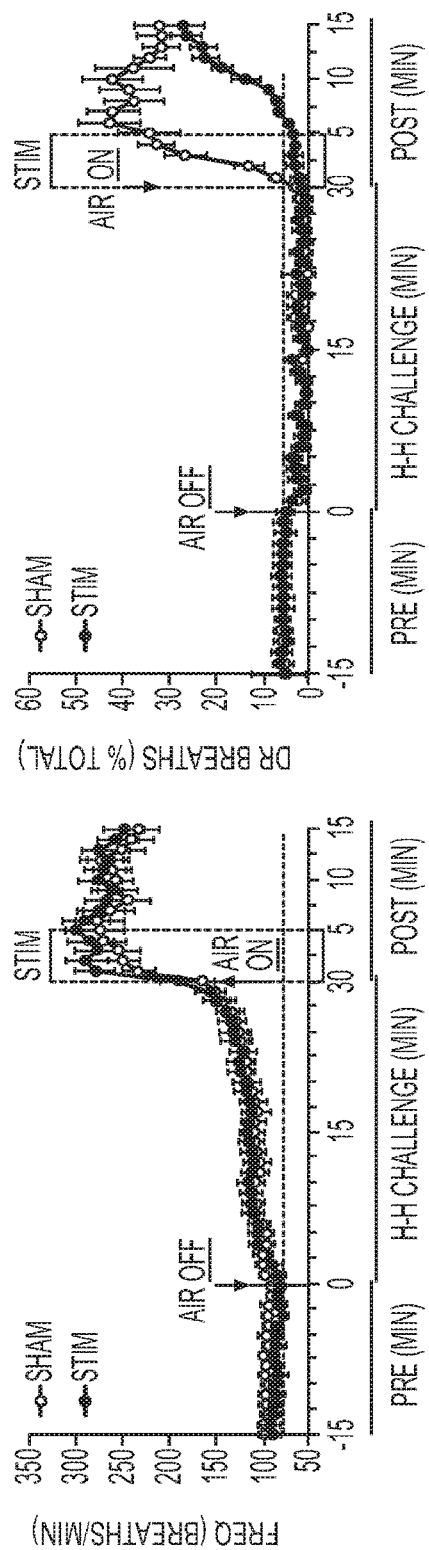
FIG. 4A: Changes in frequency of breathing and the amount of disordered breaths (DR breaths) expressed as a % of total breaths before, during and after a hypoxic-hypercapnic gas challenge in freely-moving Sprague-Dawley rats.

As seen in FIG. 4A, bilateral stimulation of the CSC markedly reduces the occurrence of disordered breathing, including apneas, in rats that upon return to room-air following a hypoxic-hypercapnic (H—H) gas challenge (Indicated as "Post" in FIG. 4A).

Figure 4B:
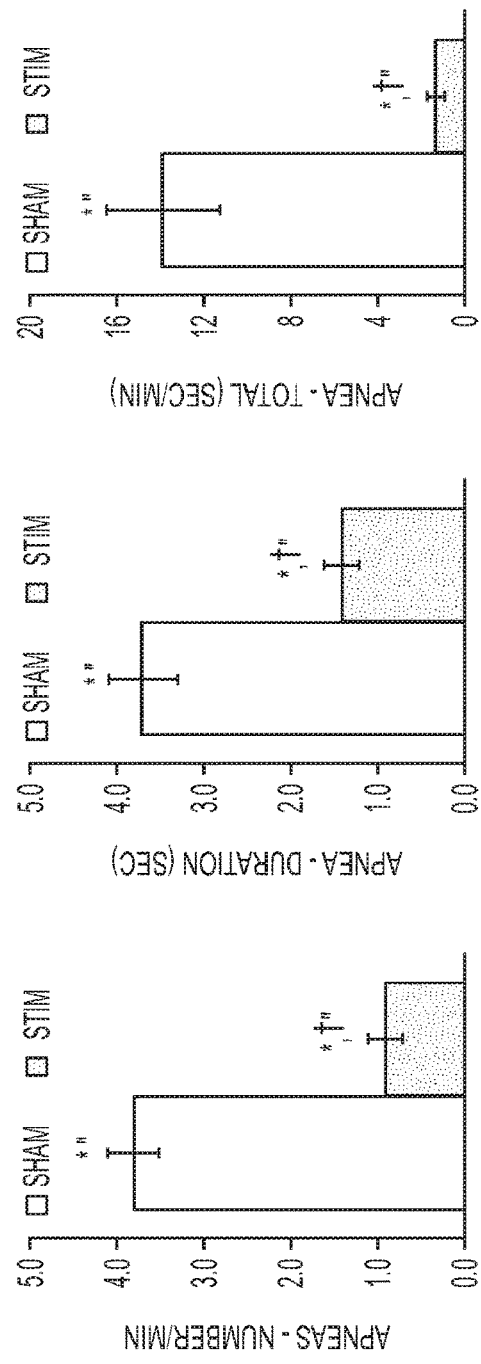
FIG. 4B: The frequency, duration and aggregate time of apnoeic episodes. The timing of the 5 min sham electrical simulation (SHAM) or actual 2.5 Hz stimulation (10V, 2 ms) of both cervical sympathetic chains are shown (STIM). The data are shown as mean±SEM. There were 15 rats in each group. *$P<0.05$, significant change from Pre. †$P<0.05$, STIM versus SHAM.

FIG. 4B shows that the frequency of apnoeas is greatly reduced as a result of bilateral CSC stimulation, as is the duration of each apnoeic episode. This results in a greatly reduced aggregate time spent in an apnoeic state.

Bilateral CSC/SCG Stimulation Improves Cardioventilatory Performance and Decreases Upper Airway Resistance In an alternative animal model (anaesthetised spontaneously hypertensive rats (SHR)), bilateral CSC stimulation resulted in a decrease in mean arterial blood pressure (FIG. 5A). Bilateral stimulation also resulted in an increase in diaphragmatic tone (an increase in diaphragm EMG activity) and an increase in genioglossus tone (an increase in genioglossus EMG activity) (FIGS. 5B and 5C). These effects were dose-dependent according to frequency of the stimulation, with 10 Hz providing the greatest effect of the frequencies tested. Such changes in diaphragmatic and genioglossus tone are indicative of improved respiratory rate and a retracted tongue, respectively. Bilateral stimulation also resulted in a decrease in upper airway resistance (FIG. 5D), a further measure of improved breathing patterns.

To further validate these findings, bilateral CSC stimulation was performed in an additional animal model. Hypoxic challenge of anaesthetised Zucker-fat rats is a recognised model of obstructive sleep apnoea.

Figure 6A:
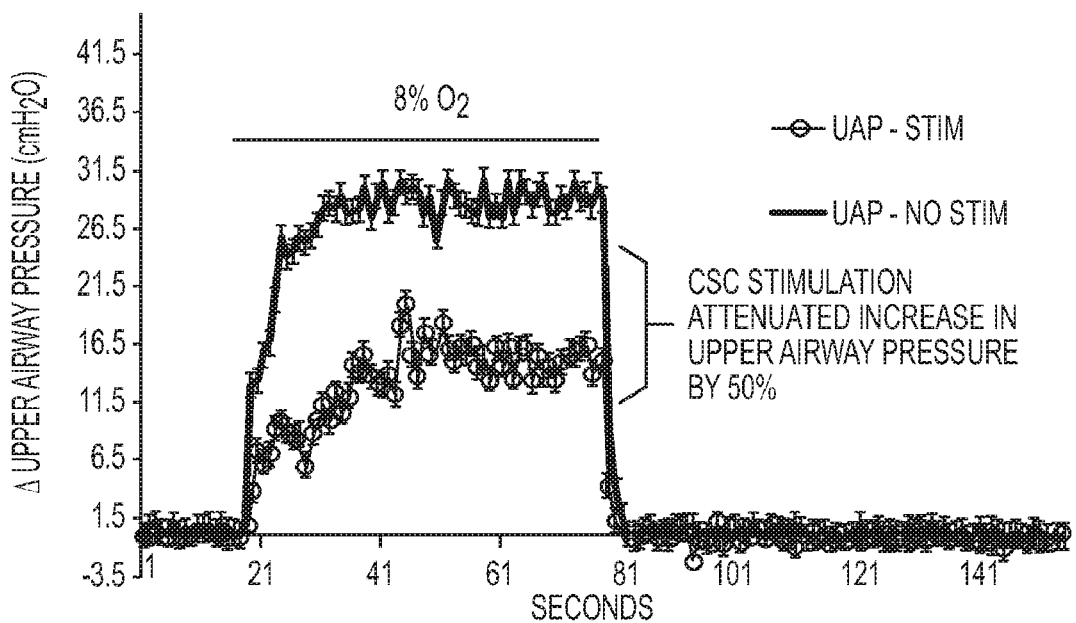
FIG. 6A: Effects of bilateral stimulation (5 Hz, 0.8 mA, 2 ms) of the cervical sympathetic chain (CSC) on the change in upper airway pressure (UAP) of anesthetized Zucker-fat rats (12 weeks of age, 450-500 g) during a 60 second hypoxic gas (10% $O_2$, 90% $N_2$) challenge. The data are presented as mean±SEM. There were 6 rats in each group.

As shown in FIG. 6A, upper airway pressure rose markedly in anesthetized Zucker-fat rats during a 60 second exposure to a hypoxic gas challenge (8% $O_2$, 92% $N_2$) (UAP-no Stimulation). This rise in upper airway pressure was markedly diminished in Zucker-fat rats in which the left and right CSCs were being stimulated (5 Hz, 0.8 mA, 2 ms) during the hypoxic challenge.

Figure 6B:
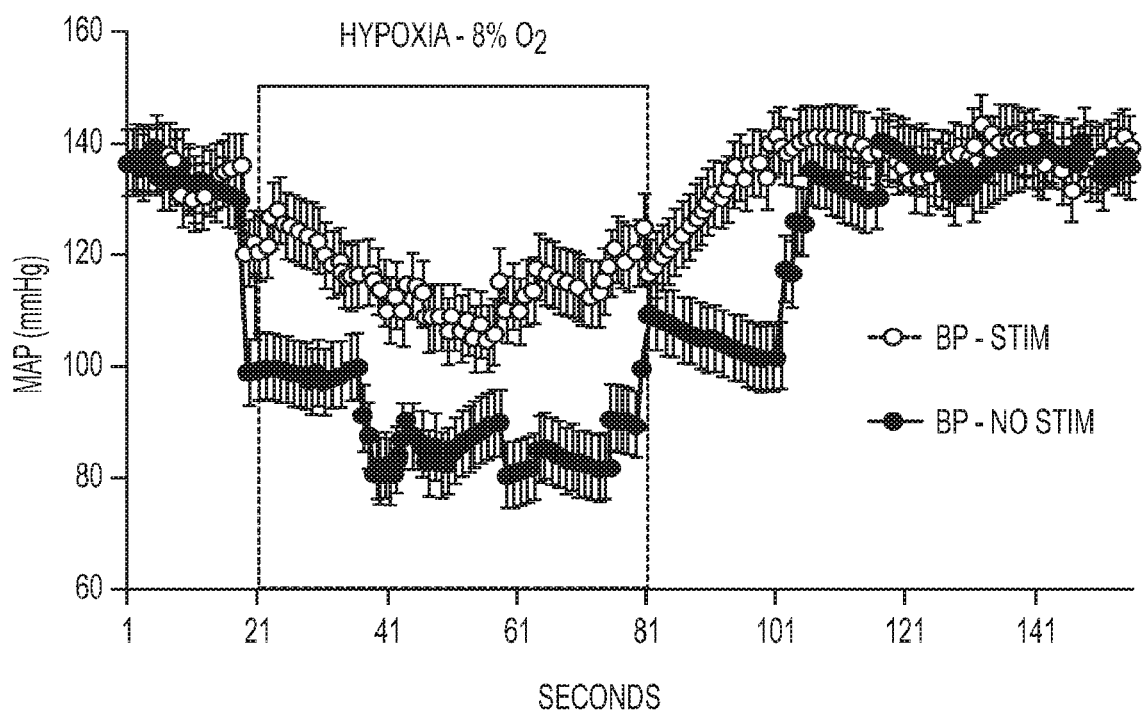
FIG. 6B: Effects of bilateral stimulation (7.5 Hz, 0.8 mA, 2 ms) of the cervical sympathetic chain (CSC) on the change in mean arterial blood pressure (MAP) of anesthetized Zucker-fat rats (16 weeks of age, 800+ grams) during a 60 second hypoxic gas (10% $O_2$, 90% $N_2$) challenge. The data are mean±SEM. There were 6 rats in each group.

Similarly, FIG. 6B shows that mean arterial blood pressure (MAP, BP-no Stimulation) fell markedly in anesthetized Zucker-fat rats during a 60-second exposure to a hypoxic challenge (8% $O_2$, 92% $N_2$). This drop in blood pressure was markedly diminished in Zucker-fat rats in which both CSCs were being stimulated (7.5 Hz, 0.8 mA, 2 ms) during the hypoxic challenge.

Figure 7:
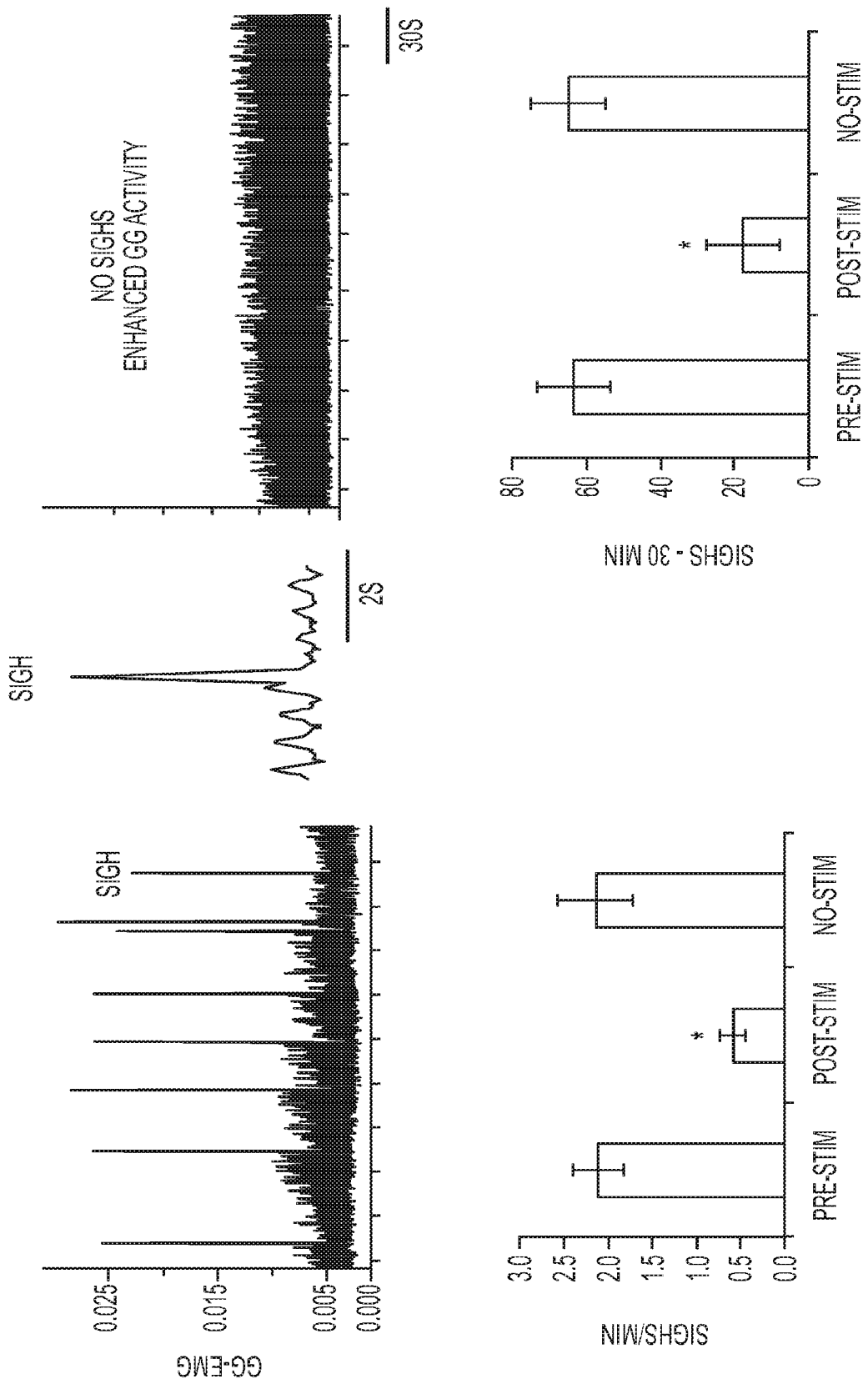
FIG. 7: Genioglossus muscle EMG (GG-EMG) activity in anesthetized Zucker-fat rats (n=6, 16 weeks of age, 800+ grams) before and 3 hours after bilateral electrical stimulation (7.5 Hz, 0.8 mA) of the cervical sympathetic chains. The data are presented as mean±SEM. *$P<0.05$, post-stimulation versus pre-stimulation or no stimulation.

Further evidence of improved ventilatory performance as a result of CSC stimulation is shown in FIG. 7. In particular, control anesthetized Zucker-fat rats display a substantial number of sighs (periods of increased respiratory effort) as defined by changes in genioglossus muscle EMG (GG-EMG; FIG. 7, top left panel). As seen in FIG. 7 (top right panel), GG-EMG was increased (positive impact on the tongue) and the incidence of sighs was markedly diminished for up to 3 hours after bilateral CSC stimulation (1 min, 7.5 Hz, 0.8 mA, 2 ms).

Figure 8:
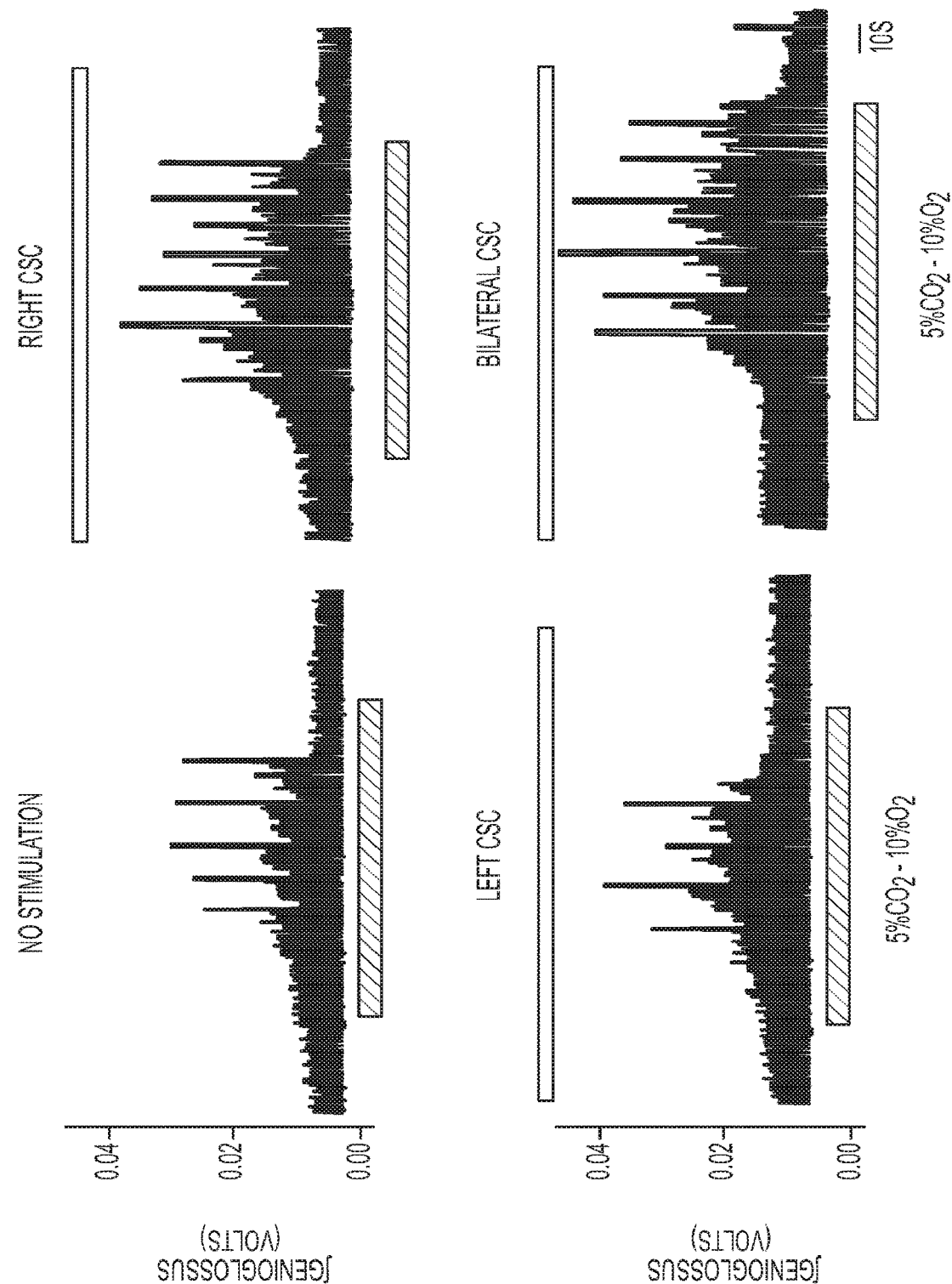
FIG. 8: Changes in genioglossus muscle EMG (GG-EMG) activity in anesthetized Zucker-fat rats (16 weeks of age, 800+g) during exposure to a hypoxic-hypercapnic gas challenge (10% O2, 5% CO2, 85% $N_2$) without and with unilateral or bilateral electrical stimulation of the cervical sympathetic chain (CSC).

Bilateral and Unilateral CSC Stimulation Promotes Retraction of the Tongue and Increases Opening of the Airway Unilateral and bilateral CSC stimulation (0.8 mA 7.5 Hz, 2 ms) markedly augmented genioglossus-EMG (GG-EMG) activity during hypoxic-hypercapnic gas challenge (10% O2, 5% CO2, 85% N2) in Zucker-fat rats (FIG. 8). Increased GG-EMG activity promotes contraction of the tongue, further validating that CSC stimulation enhances opening of the airway.

Figure 9A:
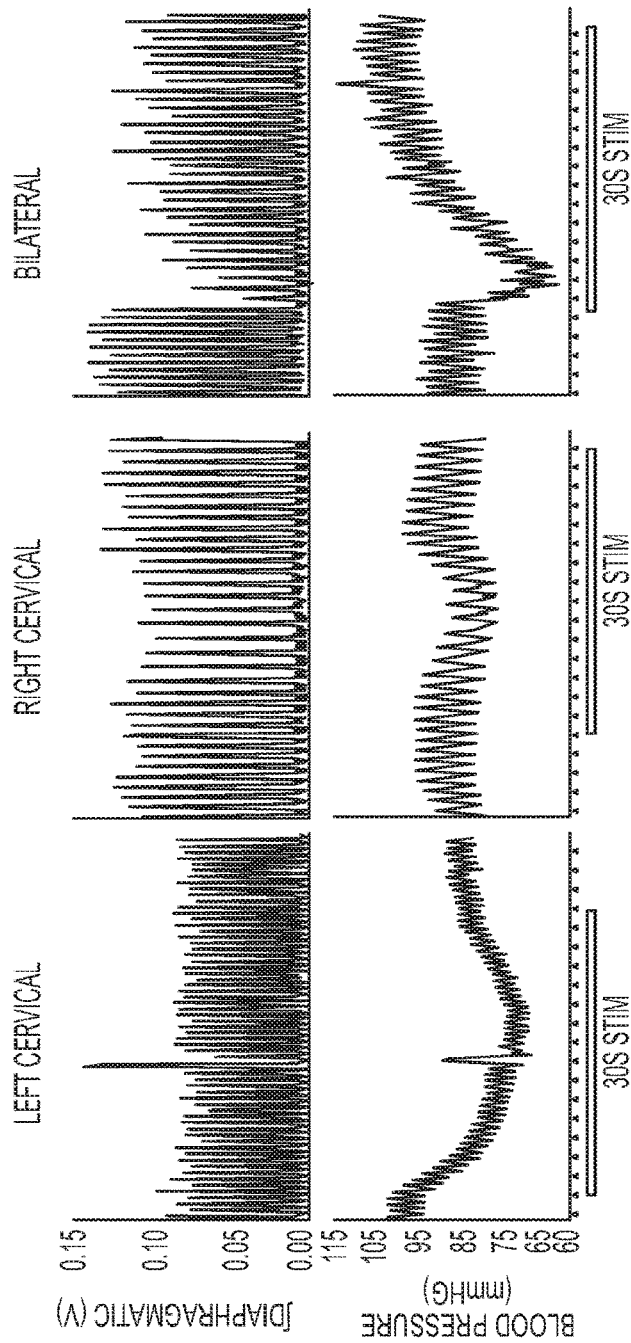
FIG. 9A: Changes in diaphragmatic EMG activity (top trace) and arterial blood pressure (bottom trace) in in an anesthetized Zucker-fat rat elicited by electrical stimulation (0.8 mA, 7.5 Hz for 30 seconds) of the left, right or both cervical sympathetic chains (CSCs).

Unilateral Left, Unilateral Right, and Bilateral Stimulation can be Used to Elicit a Differential Response A surprising finding was that by stimulating the left CSC only, the right CSC only, or both, the induced response could be tailored to result in improvements in different parameters. As shown in FIG. 9A, mean arterial blood pressure (MAP, bottom trace) fell dramatically in Zucker-fat rats upon stimulation of the left CSC (FIG. 9A, left panel, bottom trace). MAP fell minimally with right CSC stimulation (FIG. 9A, middle panel, bottom trace), and combined left and right CSC stimulation caused a transient fall in MAP that was followed by a sustained increase (FIG. 9A, right panel, bottom trace).

Figure 9B:
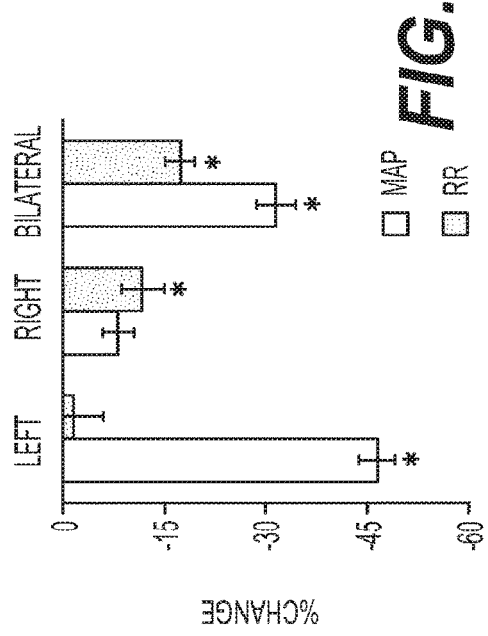
FIG. 9B: Summary of changes in mean arterial blood pressure (MAP) and respiratory rate (RR) elicited by left, right or bilateral stimulation of the CSCs in Zucker-fat rats (16 weeks of age, 800+g, from Charles Rivers). The data are mean±SEM of 5 rats. *$P<0.05$, significant response.

In contrast, right CSC stimulation had a greater effect on breathing (FIG. 9A, diaphragmatic-EMG; top trace, middle panel) than left CSC stimulation (FIG. 9A, top trace, left and centre panel). It is noted that this fall in respiratory rate was in response to a highly beneficial increase in tidal volume (data not shown). FIG. 9B summarizes these findings from Zucker-fat rats and supports the conclusions that differential stimulation of the left and right CSCs, or both, can elicit different responses.

Figure 10:
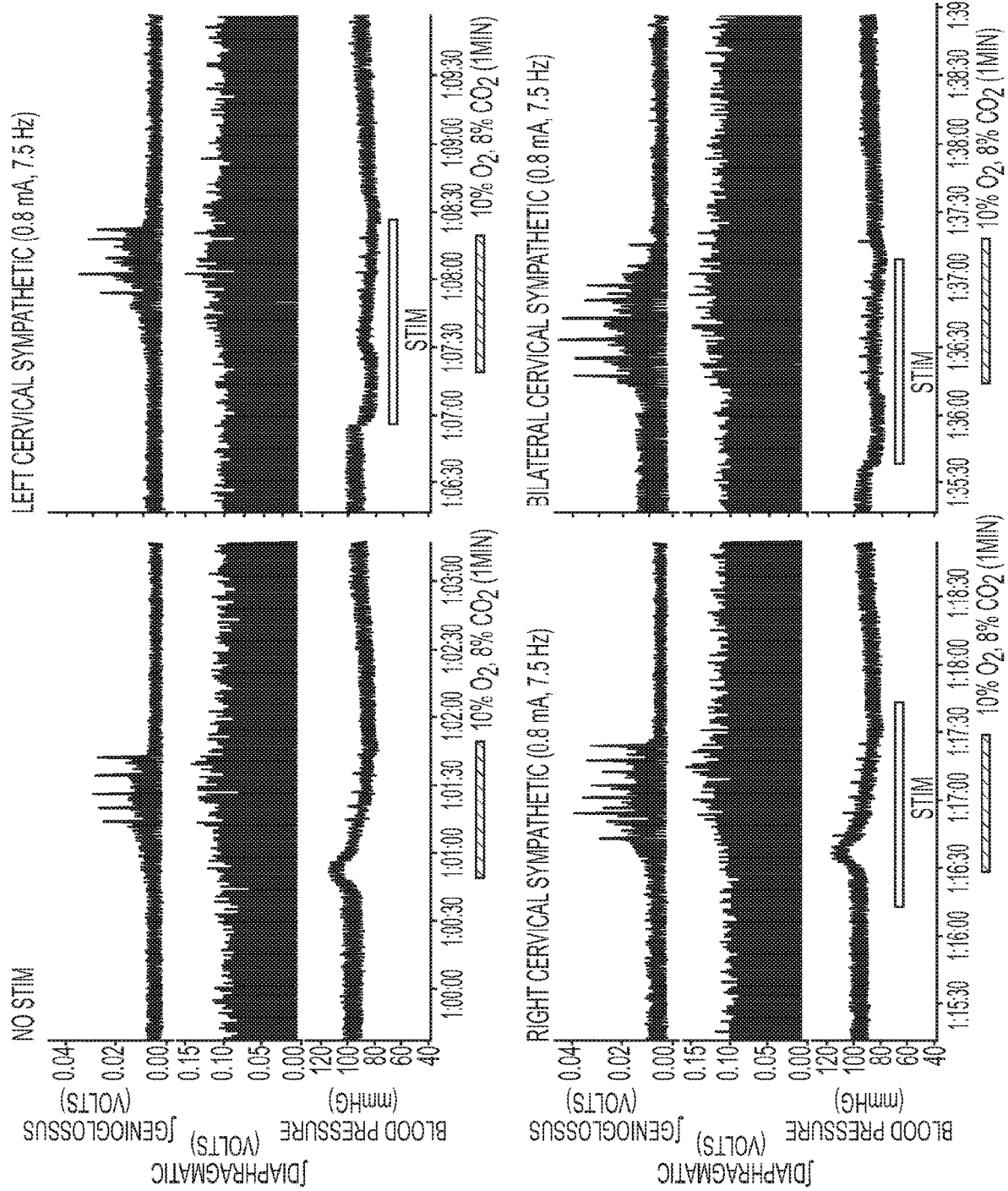
FIG. 10: Changes in genioglossus-EMG, diaphragmatic-EMG and blood pressure elicited by a hypoxic-hypercapnic gas challenge (10% O2, 8% CO2, 82% N2) in an anesthetized Zucker-fat rat (16 weeks of age, 800+g, from Charles Rivers) with and without electrical stimulation of the left, right or both cervical sympathetic chains.

The ability of unilateral left, unilateral right, and bilateral stimulation of the CSC to elicit different responses was also observed in relation to muscle activity. As seen in FIG. 10 (top left panel), the exposure of a Zucker-fat rat to a H—H gas challenge (10% $O_2$, 5% $CO_2$, 85% $N_2$) causes a small amount of genioglossus-EMG activity, consistent with retraction of the tongue (FIG. 10, top trace, left panel). H—H gas challenge also results in an increase in diaphragmatic-EMG indicative of an increase in breathing frequency (left panel, middle trace) as well as a biphasic change in blood pressure (left panel, bottom trace). As seen in the other panels of FIG. 10, concurrent stimulation of the left, more so the right, and especially bilateral electrical stimulation of the CSCs markedly enhances the genioglossus-EMG responses (indicative of increased retraction of the tongue) and diminishes the changes in blood pressure during H—H challenge.

The finding that CSC stimulation promotes opening of the upper airway by retraction of the tongue was entirely unexpected, as the CSC was not predicted to control skeletal muscle such as the genioglossus. The observed effects further strengthen the evidence that unilateral (left or right) and bilateral electrical stimulation of the CSC is an effective therapy for sleep apnoea since both central and obstructive sleep apnoea in humans heavily involves the malposition of the tongue over the airway which blocks airflow.

CSC Stimulation is Effective at a Number of Signal Amplitudes

Figure 11:
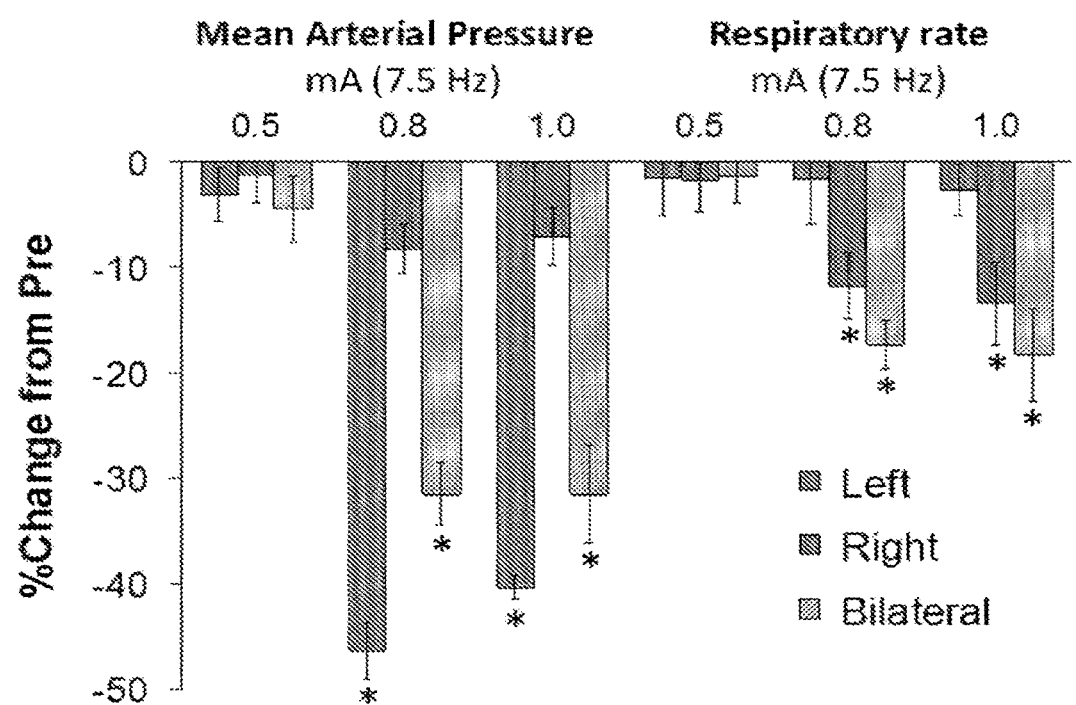
FIG. 11: Changes in mean arterial blood pressure and respiratory rate in anesthetized Zucker-fat rats (n=5, 16 weeks of age, 800+g, from Charles Rivers) elicited by electrical stimulation (0.5, 0.8, & 1.0 mA, 7.5 Hz for 30 sec) of the left, right or both cervical sympathetic chains. The data are mean±SEM. *$P<0.05$, significant response.

As shown in FIG. 11, the observed improvements in blood pressure (Mean Arterial Pressure (MAP)) and respiratory rate as a result of CSC stimulation could be induced across a range of current amplitudes. A signal having a current amplitude of 0.5 mA elicited a small effect; a signal having a current amplitude of 1.0 mA elicited a greater effect; the most efficacious signal was one having a current amplitude of 0.8 mA.

Hypoglossal Stimulation is Less Effective than CSC Stimulation

Figure 12:
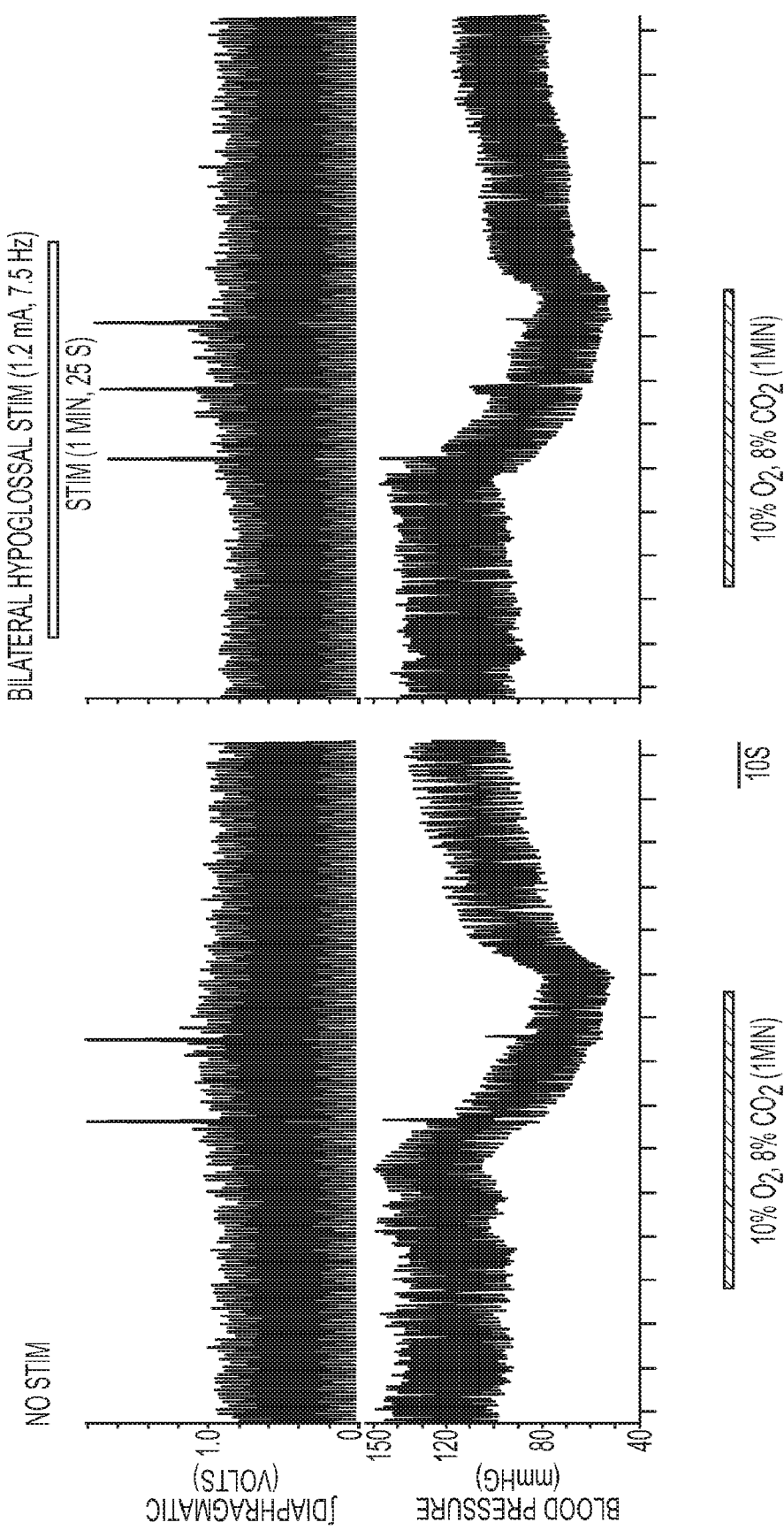
FIG. 12: Lack of effect of bilateral stimulation of the hypoglossal nerve on the increases in diaphragmatic-EMG and falls in arterial blood pressure that occur during hypoxic-hypercapnic (H—H) gas challenge (10% $O_2$, 5% $CO_2$, 85% $N_2$) in a Zucker-fat rat.

Attempts to treat sleep apnoea in the prior art have included stimulation of the hypoglossal nerve. However, FIG. 12 shows that unlike CSC stimulation, stimulation of the hypoglossal nerve does not affect the increases in diaphragmatic-EMG (top trace) and falls in arterial blood pressure (bottom trace) in Zucker-fat rats that occur during hypoxic-hypercapnic gas challenge (10% $O_2$, 5% $CO_2$, 85% $N_2$) (FIG. 12, left panel control rats; right panel hypoglossal stimulation). CSC stimulation thus provides a more effective treatment for sleep apnoea.

Example 2

Figure 13:
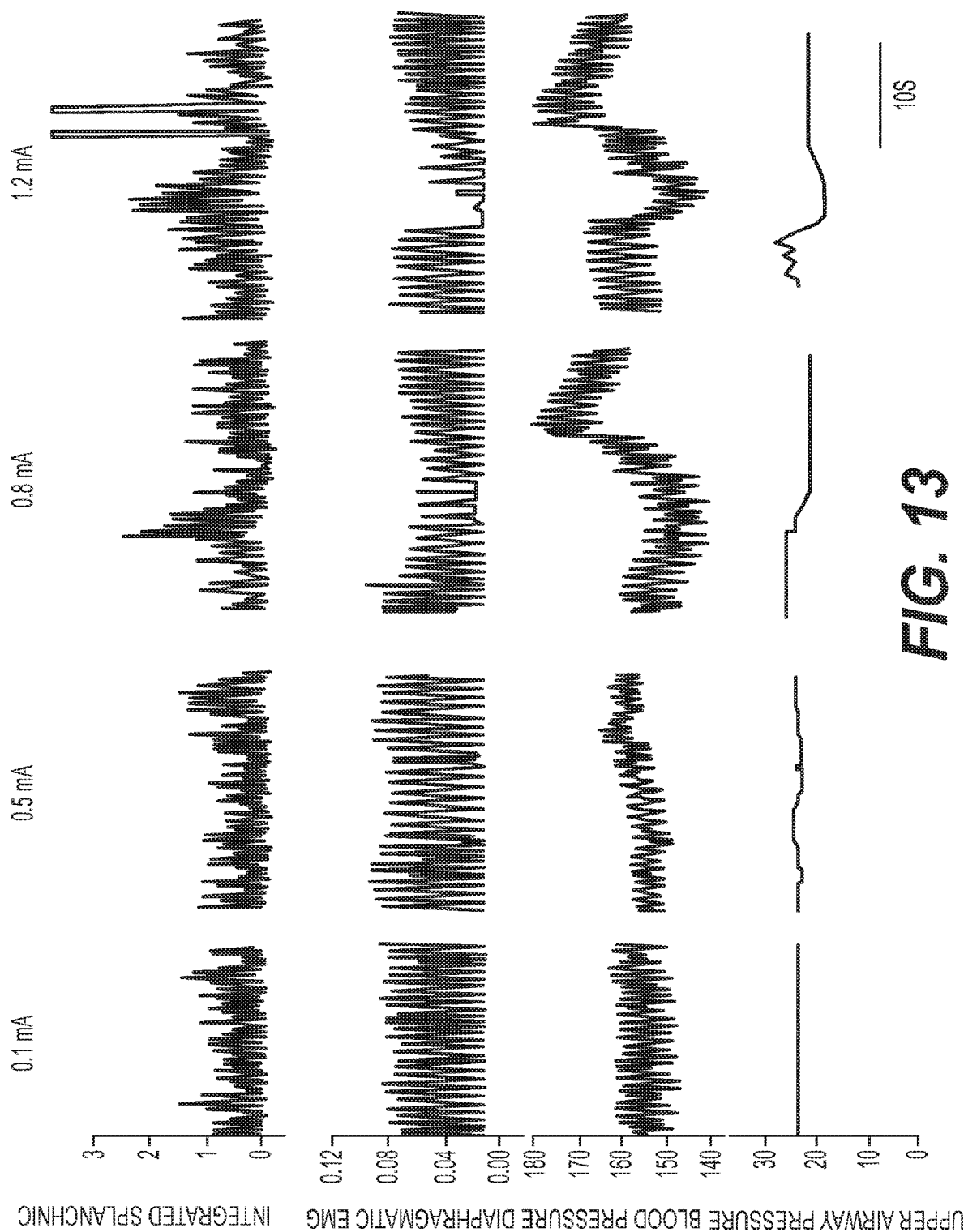
FIG. 13: Bilateral stimulation of CSC (bipolar electrodes) reduces upper airway pressure and affects cardio-respiratory output in anesthetized Zucker fat rats (n=5).

Anaesthetised Zucker fat rats (15-18 wks) underwent bilateral stimulation of the CSC (using cuff electrodes). The signal applies was 5 Hz, 2 ms pulse width, with current of 0.1 mA, 0.5 mA, 0.8 mA or 1.2 mA. The results are shown in FIG. 13. 0.8 mA current resulted in a decrease in airway pressure and an increase in blood pressure. Current of 1.2 mA resulted in a marked decrease in airway pressure as well as decrease in blood pressure.

Figure 14A:
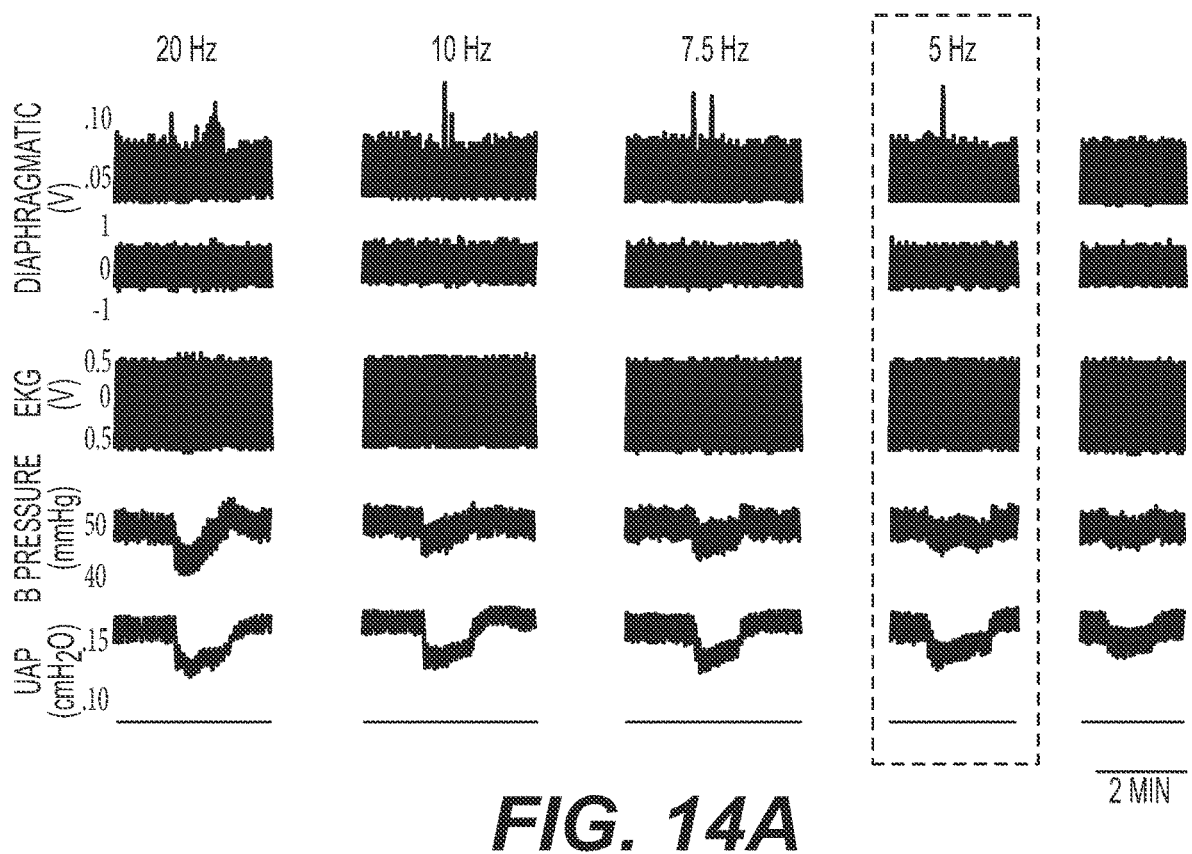
FIGS. 14A-14B: Bilateral stimulation of CSC. Changes in stimulation frequency differentially impacted blood pressure and upper airway pressure (n=5). Percentage change calculated versus each rat prior to stimulation.
Figure 14B:
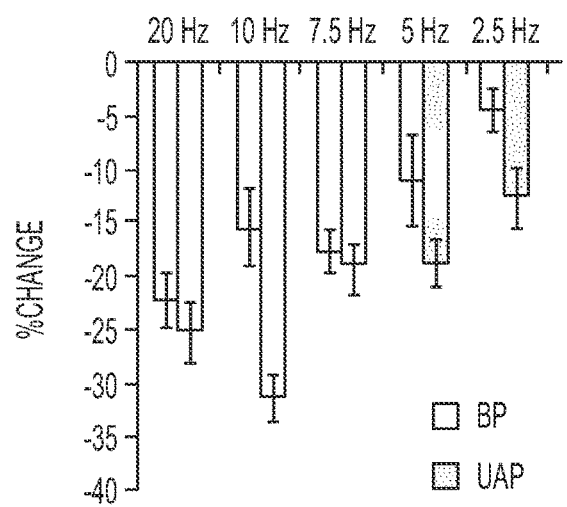

Changes in stimulation frequency also differentially impacted blood pressure and upper airway pressure. High frequency stimulations decrease blood pressure sharply versus lower frequencies—for example, 2.5 Hz resulted in only a small drop in blood pressure versus more significant falls when higher frequencies were used (FIGS. 14A-14B). Bilateral stimulation using 0.5 mA, 2 ms pulse width, 5 Hz was determined to result in upper airway pressure being decreased significantly without blood pressure dropping significantly (FIGS. 14A-14B).

Changes in stimulation pulse width also differentially impacted blood pressure and upper airway pressure. High pulse width stimulations decrease blood pressure sharply versus lower pulse widths. (FIG. 15) Bilateral stimulation using 0.5 mA, 5.0 Hz, 0.2 ms pulse width was determined as resulting in upper airway pressure decreasing significantly without blood pressure dropping significantly (FIG. 15).

Chronic Stimulation

Methods: All surgical procedures were performed in a sterile surgical suite with Male Zucker Fat Rats (15-20 wks) were administered 4-5% isoflurane via vaporizer and nosecone. Once anesthetized isoflurane was reduced to 1-2%. The anesthetic plane was monitored via toe pinch and respiration while surgical procedures are conducted. An incision was made between the eyes to between the ears to reveal the skull. 3 screws were drilled in the skull to help secure the stimulating headcap. The headcap was reinforced with dental cement. The wired cuff electrodes were trochared next to the cervical sympathetic chain. Once the CSC was isolated and placed into the cuff, Tisseel, a fibrinogen, was placed around the electrode/nerve interface to secure the electrode. After surgery rats were immediately placed in their home cages in a warming cabinet set at 30° C. for up to an hour. After that rats were housed individually on soft bedding and given pellets on the floor for 7 days. Surgical wounds were observed daily and animals weighed. Dry cereal made into a paste and rehydration fluid was made available per vet consult. All external skin sutures were removed after 2 weeks. The animal was used for conscious studies 2 weeks after surgery or until a return to baseline weight.

Results

Figure 16A:
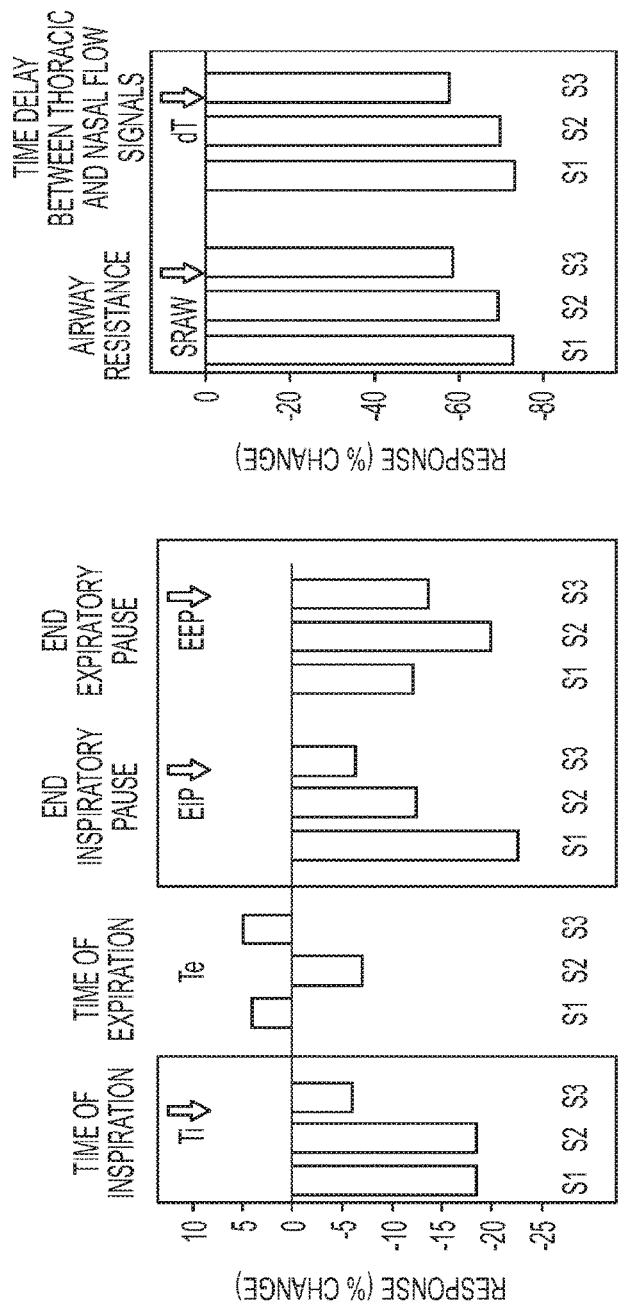
FIGS. 16A-16B: Double plethysmography chambers were used to assess changes in airway resistance in animals after bilateral CSC stimulation (0.5 mA, 5 Hz, 0.2 ms, 5 min recovery between stimuli) (conscious Zucker Fat (14 wks) male rats, n=2). Response (% Change) was calculated by comparing to baseline values, each animal was a control for itself. S1, S2 and S3 are each separate stimulation events.

Double plethysmography chambers were used to assess changes in airway resistance in animals after stimulation. Bilateral CSC stimulation (0.5 mA, 5 Hz, 0.2 ms, 5 min recovery between stimuli) showed decreases in (FIG. 16A): upper airway resistance (Sraw); time delay between thoracic and nasal flow signals (dT); time of inspiration (TI); end expiratory pause (EEP); and end inspiratory pause (EIP) (FIG. 16A). Response (% Change) was calculated by comparing each rat to baseline values for the same rat prior to first stimulation. S1-S3 represent 3 separate stimulations 5 minutes apart.

Figure 16B:
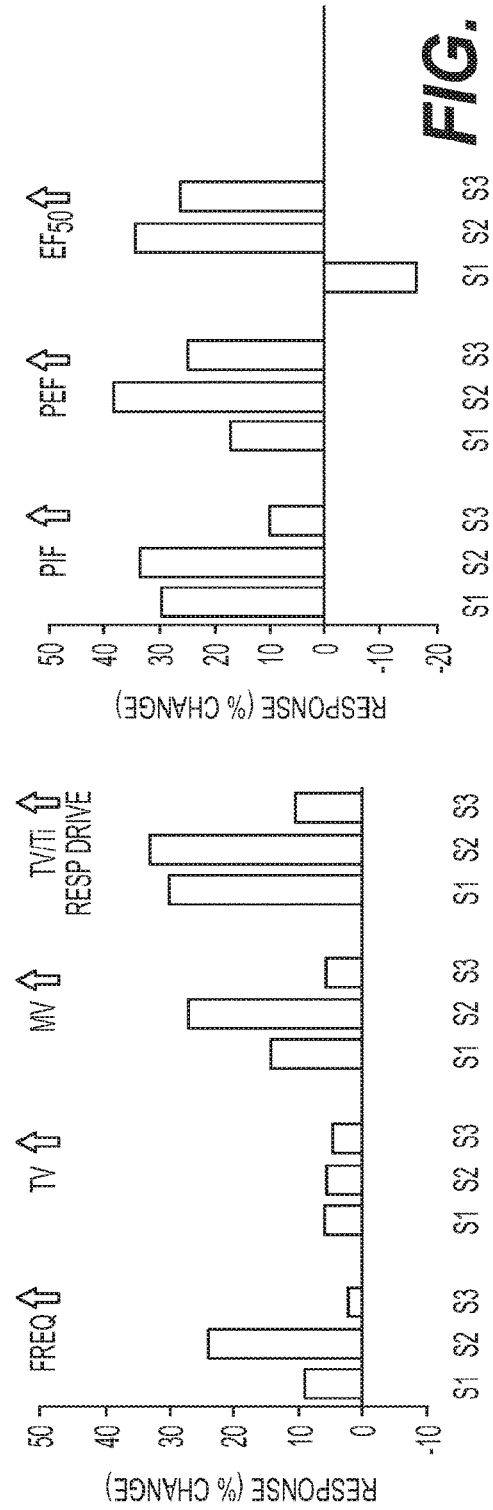

The same bilateral stimulation also resulted in an increase in (FIG. 16B): respiratory frequency (Freq); tidal volume (TV); minute ventilation (MV); central respiratory drive defined by (TV/TI); peak inspiratory flow (PIF); peak expiratory flow (PEF); and bronchodilation (EF 50) (FIG. 16B). Response (% Change) was calculated by comparing each rat to baseline values for the same rat prior to stimulation. S1-S3 represent 3 separate stimulations 5 minutes apart.

Figure 17:
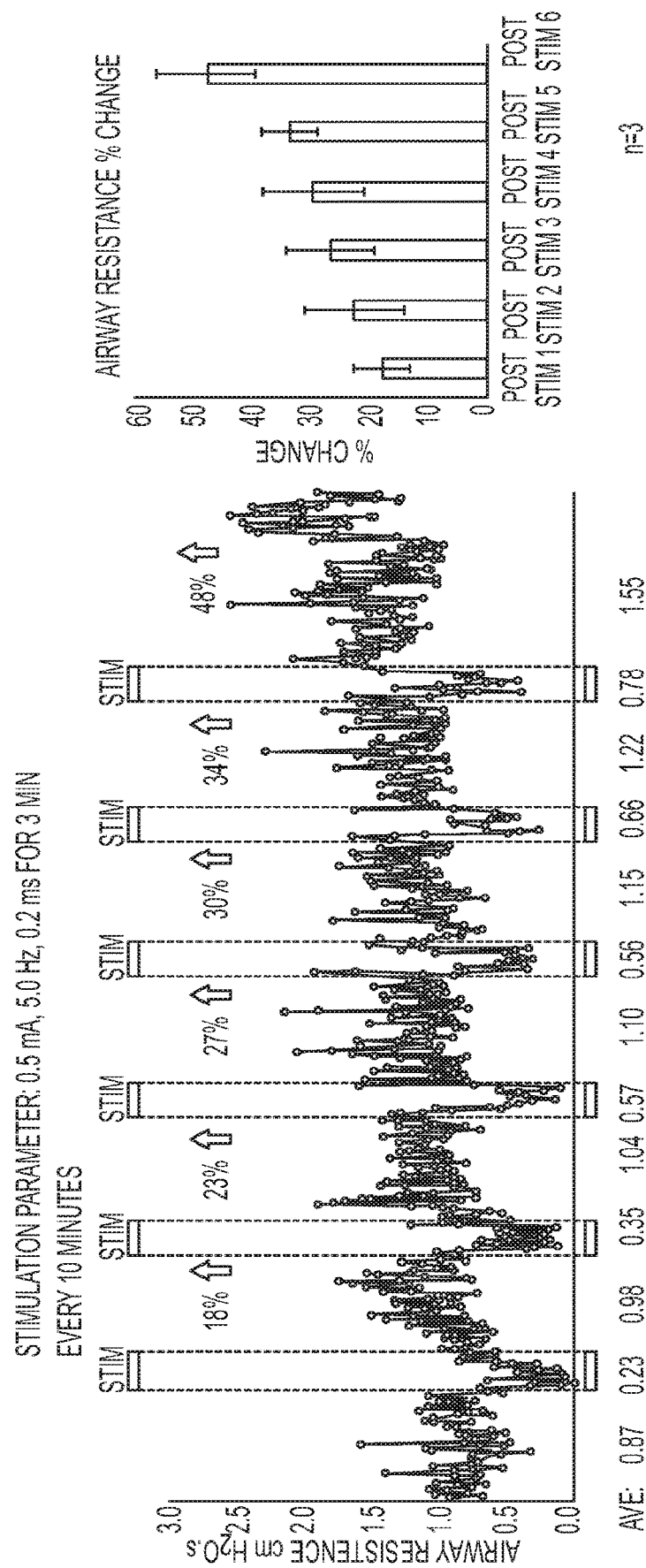
FIG. 17: Airway resistance trace during continuous bilateral CSC stimulation (0.5 mA, 5 Hz, 0.2 ms) for 3 minutes every 10 minutes. Percentage change calculated versus each rat's own baseline value.

Continuous bilateral stimulation (0.5 mA, 5.0 Hz, 0.2 ms) for 3 minutes every 10 minutes decreased airway resistance during stimulation. Following stimulation for 3 minutes, airway resistance was increased relative to baseline (FIG. 17).

Figure 18:
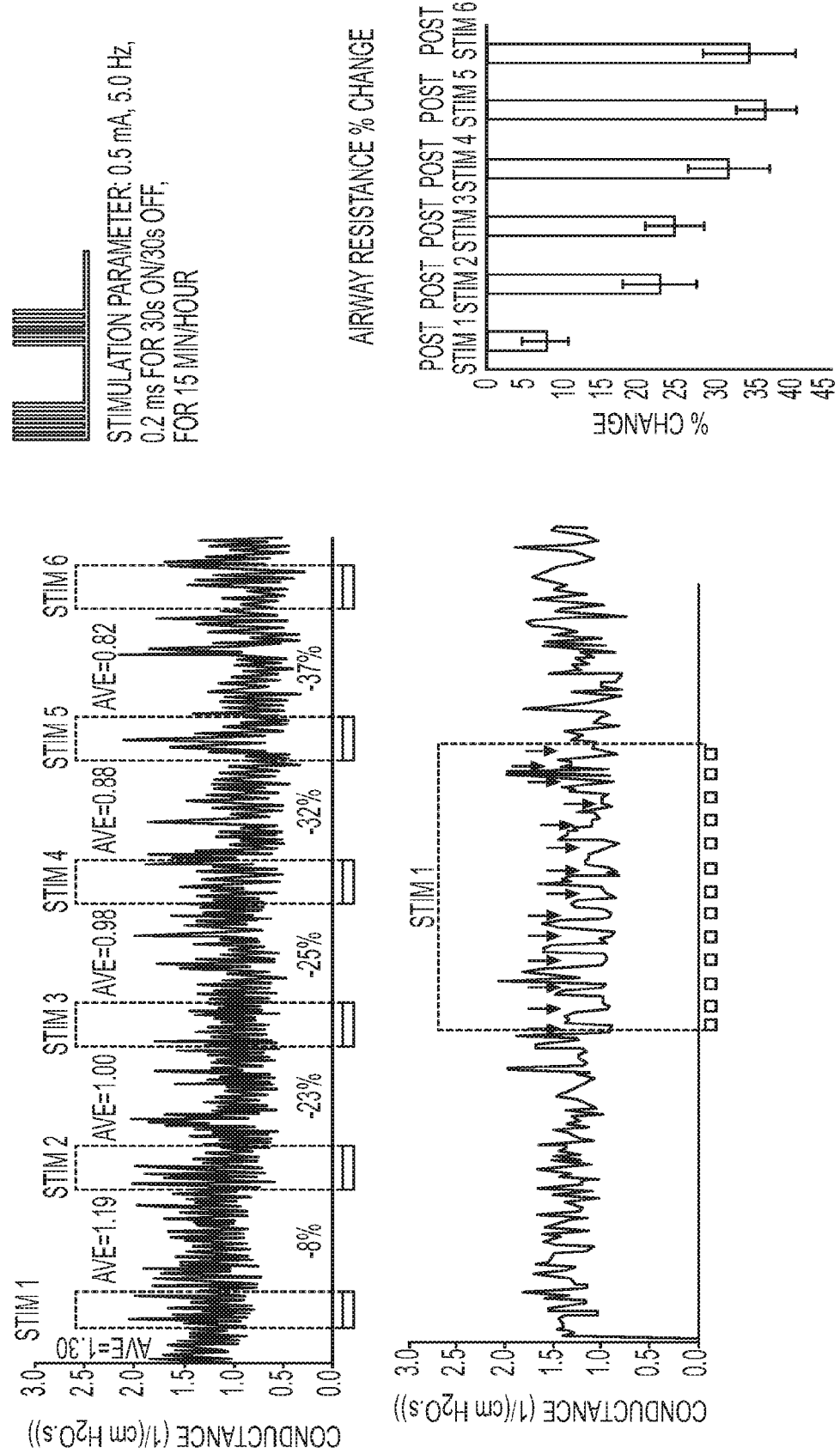
FIG. 18: Airway resistance trace during intermittent bilateral CSC stimulation (0.5 mA, 5 Hz, 0.2 ms) of 30 s on, 30 s off for 15 minutes every hour. Protocol was applied for 6 hours. Percentage change calculated versus each rat's own baseline value.

Intermittent stimulation (bilateral, 0.5 mA, 5.0 Hz, 0.2 ms) in which the signal was applied 30 s on and 30 s off resulted in a marked decrease in airway resistance both during stimulation and progressively after each stimulation (FIG. 18). Intermittent stimulation was applied for 15 minutes every hour, for 6 hours.

Whole body plethysmography was used to assess the effect of intermittent stimulation on the number of disordered breaths. Bilateral acute intermittent CSC stimulation (0.5 mA, 5 Hz, 0.2 ms) was applied to conscious freely moving Zucker Fat (14 wk) male. As shown in FIG. 19 (left-hand bars), stimulation resulted in increases in: Tidal Volume (TV); Minute Ventilation (MV); Central Respiratory Drive defined by (TV/TI).

Figure 20:
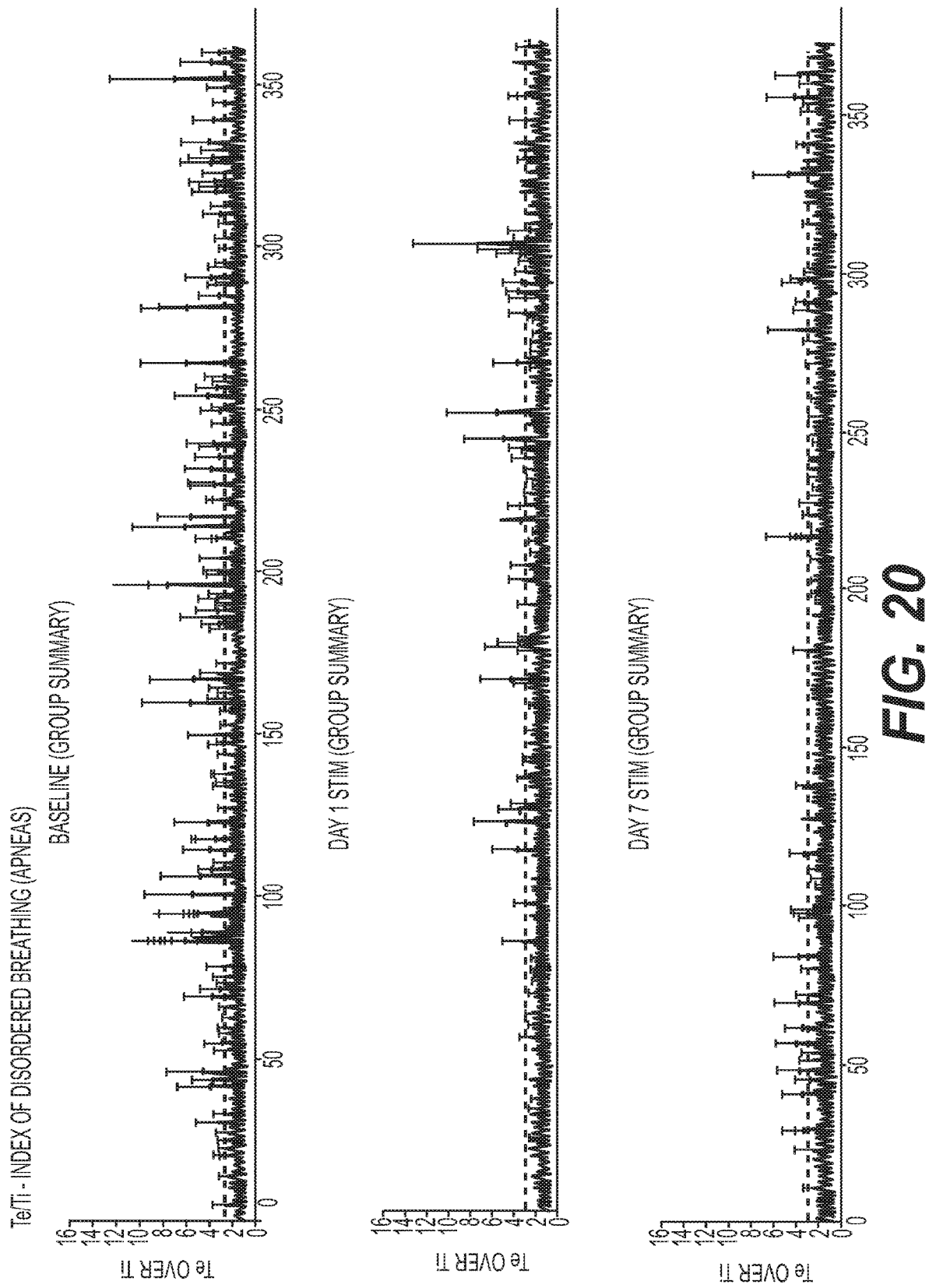
FIG. 20: Disordered breathing levels before bilateral intermittent CSC stimulation (0.5 mA, 5 Hz, 0.2 ms), after 1 day and after 7 days of intermittent stimulation. Number of disordered breaths defined by breaths that were two times as long as the average expiration time (Te) over inspiration time (Ti) (Te/Ti). Conscious freely moving Zucker Fat (14 wks) male (n=3).
Figure 20:
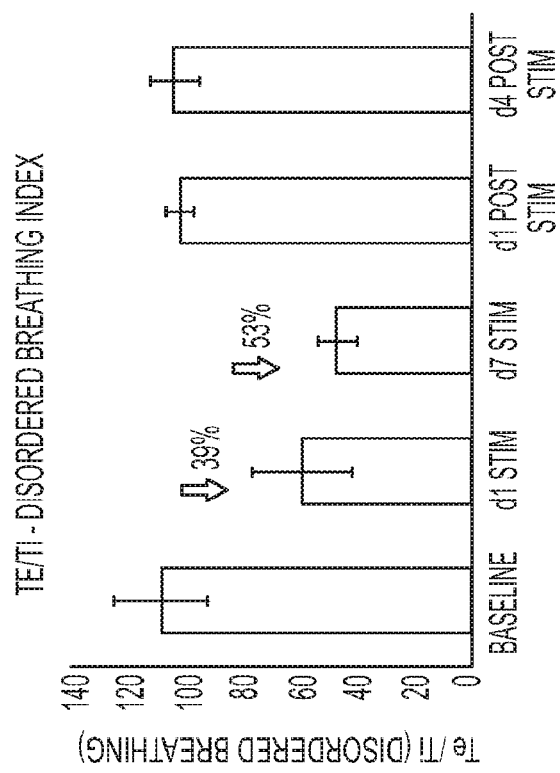

The observed reduction in disordered breaths (apnoeas) following intermittent stimulation was continued when the stimulation protocol was applied for 7 consecutive days (FIG. 19, right-hand bars, and FIG. 20). Bilateral acute intermittent CSC stimulation (0.5 mA, 5 Hz, 0.2 ms) in conscious freely moving Zucker Fat (14 wk) male were stimulated for 7 consecutive days following the acute intermittent stimulation protocol of 30 s on/off for 15 minutes every hour and were able to reduce the number of disordered breaths (defined by breath that were two times as long as the average Te/Ti) during the week of stimulation (FIG. 20) (n=3). It was reduced by 39% on the first day and 53% on the 7th day. The number of disordered breaths returned after the stimulation protocol ended.

The invention claimed is:

1. An apparatus for treating sleep apnea in a subject, the apparatus comprising:
   i. at least two implantable neural interfacing elements each having one or more electrodes, wherein one of the at least two implantable neural interfacing elements is configured to be in signaling contact with at least one of a left cervical sympathetic chain (CSC), a left superior cervical ganglion (SCG) or postganglionic branch thereof to induce a change in a first parameter associated with sleep apnea and wherein the other one of the at least two implantable neural interfacing elements is configured to be in signaling contact with at least one of a right cervical sympathetic chain (CSC), a right superior cervical ganglion (SCG) or postganglionic branch thereof to induce change in a second parameter associated with sleep apnea; and
   ii. a controller operably coupled to the at least two implantable neural interfacing elements, the controller causes the at least two implantable neural interfacing elements to deliver electrical signals that increase localized sympathetic activity of the left CSC, left SCG or postganglionic branch thereof and the right CSC, the right SCG or postganglionic branch thereof,
   wherein the increased sympathetic activity of at least one of the CSC, SCG or postganglionic branch ameliorates sleep apnea in the subject, and further wherein the electrical signals induce changes to the first parameter and the second parameter and modulate different aspects of sleep apnea.

2. The apparatus of claim 1, wherein at least one of the one or more electrodes is a cuff electrode.

3. The apparatus according to claim 1, wherein one of the electrical signals is initiated at a first frequency and then altered to a second frequency, wherein (a) the first frequency is higher than the second frequency; or (b) the first frequency is lower than the second frequency.

4. The apparatus according claim 1, wherein the controller is configured to cause at least one of the electrical signals to be delivered intermittently.

5. The apparatus according to claim 4, wherein the controller causes at least one of the electrical selected signals to be delivered for a first time period, then stopped for a second time period, then reapplied for a third time period, then stopped for a fourth time period, wherein a duration of each of the first, second, third and fourth time periods is selected from: 0.8 s-2 min, 0.8 s-30 s, 0.8 s-10 s, 0.8 s-5 s, 0.8-2 s, 10 s-2 min, 30 s-2 min, and 30 s-1 min.

6. The apparatus according to claim 1, wherein the increase in localized sympathetic activity in at least one of the CSC, SCG or postganglionic branch thereof produces one or more of: a decrease in duration of apneic episodes, a decrease in frequency of apneic episodes, a decrease in blood pressure, a decrease in respiratory rate, an increase in tidal volume, a decrease in upper airway resistance, an increase in diaphragmatic muscle activity, an increase in genioglossus muscle activity, and an increase in central respiratory drive.

7. The apparatus according to claim 1, wherein the increase in localized sympathetic activity in at least one of the CSC, SCG or postganglionic branch thereof results in at least one of an increase in tidal volume, a decrease in upper airway resistance, an increase in diaphragmatic muscle activity and an increase in genioglossus muscle activity.

8. The apparatus according to claim 1, wherein the apparatus further comprises a detector to detect one or more physiological parameters in the subject, wherein one or more of the detected physiological parameters is selected from sympathetic tone; diaphragmatic tone; genioglossus tone; blood pressure; respiratory rate; tidal volume; upper airway resistance; and central respiratory drive.

9. The apparatus according to claim 8, wherein the controller is coupled to the detector, and causes at least one implantable neural interfacing element to apply an independently selected signal when the physiological parameter meets a predefined value.

10. The apparatus according to claim 1, wherein the increased localized sympathetic activity is substantially persistent.

11. The apparatus according to claim 1, wherein the increased localized sympathetic activity is temporary.

12. The apparatus according to claim 1, wherein the apparatus is suitable for full implantation into the subject.

13. An apparatus for modulating neural activity of at least one of a CSC, SCG or postganglionic branch of a subject, the apparatus comprising:
  at least two neural interfacing elements comprising one or more electrodes each neural interfacing element configured to apply an independently selected electrical signal, wherein one of the at least two implantable neural interfacing elements is configured to be in signaling contact with at least one of a left cervical sympathetic chain (CSC), a left superior cervical ganglion (SCG) or postganglionic branch thereof to induce change in a first parameter associated with sleep apnea, and wherein the other one of the at least two implantable neural interfacing elements is configured to be in signaling contact with at least one of a right cervical sympathetic chain (CSC), a right superior cervical ganglion (SCG) or postganglionic branch thereof to induce change in a second parameter associated with sleep apnea that is different from the first parameter; and
  a controller operably coupled to the at least two neural interfacing elements to provide differential stimulation, the controller controlling the electrical signals to be applied by each of the at least two neural interfacing elements, such that the electrical signals applied by the at least one neural interfacing element stimulates increased localized sympathetic activity in at least one of the CSC, SCG or postganglionic branch in the subject, and wherein the electrical signals cause improvements in the first parameter and the second parameter.

14. The apparatus of claim 13, wherein at least one of the one or more electrodes is a cuff electrode.

15. A method for increasing sympathetic activity of a subject comprising:
  implanting in the subject at least a portion of an apparatus for modulating (a) the neural activity of at least one of a left CSC, a left SCG or postganglionic branch of the subject and (b) the neural activity of at least one of a right CSC, a right SCG or postganglionic branch of the subject, the apparatus comprising:
  i. at least two neural interfacing elements for providing differential stimulation, each neural interfacing element comprising one or more electrodes, wherein one of the at least two neural interfacing elements is configured to apply an electrical signal to at least one of the left CSC, the left SCG or postganglionic branch thereof of the subject and is placed in signaling contact with at least one of the left CSC, the left SCG or postganglionic branch thereof to induce a change in a first parameter associated with sleep apnea, and further wherein the other one of the at least two neural interfacing elements is configured to apply a selected electrical signal to at least one of a right CSC, a right SCG or postganglionic branch thereof and is placed in signaling contact with at least one of a right CSC, the right SCG or postganglionic branch thereof to induce a change in a second parameter associated with sleep apnea; and
  ii. a controller operably coupled to the at least two neural interfacing elements, the controller controlling the electrical signals to be applied by each of the at least two neural interfacing elements, such that at least one neural interfacing element stimulates increased localized sympathetic activity;
  positioning one of the at least two neural interfacing elements of the apparatus in signaling contact with at least one of the left CSC, left SCG or postganglionic branch thereof of the subject;
  positioning one of the at least two neural interfacing elements neural interfacing elements of the apparatus in signaling contact with at least one of the right CSC, right SCG or postganglionic branch thereof of the subject; and
  activating the apparatus to cause an improvement in at least two of the following: a decrease in duration of apneic episodes, a decrease in frequency of apneic episodes, a decrease in blood pressure, a decrease in respiratory rate, an increase in tidal volume, a decrease in upper airway resistance, an increase in diaphragmatic muscle activity, an increase in genioglossus muscle activity, and an increase in central respiratory drive.

16. The method according to claim 15, wherein the increased localized sympathetic activity ameliorates a condition of sleep apnea in the subject.

17. The method according to claim 15, wherein an increase in localized sympathetic activity is indicated by one or more of a decrease in blood pressure, a decrease in respiratory rate, an increase in tidal volume, a decrease in upper airway resistance, an increase in diaphragmatic muscle activity, an increase in genioglossus muscle activity, and an increase in central respiratory drive.

* * * * *